United States Patent
Shimoda et al.

(10) Patent No.: US 11,572,533 B2
(45) Date of Patent: *Feb. 7, 2023

(54) QUATERNARY ALKYLAMMONIUM HYPOCHLORITE SOLUTION, METHOD FOR MANUFACTURING SAME, AND METHOD FOR CLEANING SEMICONDUCTOR WAFER

(71) Applicant: Tokuyama Corporation, Yamaguchi (JP)

(72) Inventors: Takafumi Shimoda, Yamaguchi (JP); Yuki Kikkawa, Yamaguchi (JP); Takayuki Negishi, Yamaguchi (JP); Seiji Tono, Yamaguchi (JP)

(73) Assignee: Tokuyama Corporation, Yamaguchi (JP)

( * ) Notice: Subject to any disclaimer, the term of this patent is extended or adjusted under 35 U.S.C. 154(b) by 227 days.

This patent is subject to a terminal disclaimer.

(21) Appl. No.: 17/057,207

(22) PCT Filed: May 20, 2019

(86) PCT No.: PCT/JP2019/019898
§ 371 (c)(1),
(2) Date: Nov. 20, 2020

(87) PCT Pub. No.: WO2019/225541
PCT Pub. Date: Nov. 28, 2019

(65) Prior Publication Data
US 2021/0309942 A1    Oct. 7, 2021

(30) Foreign Application Priority Data

May 23, 2018  (JP) .............................. JP2018-099223
May 23, 2018  (JP) .............................. JP2018-099224
Jun. 20, 2018  (JP) .............................. JP2018-116832

(51) Int. Cl.
*C07C 209/66*    (2006.01)
*C11D 7/32*    (2006.01)
(Continued)

(52) U.S. Cl.
CPC .......... *C11D 7/3209* (2013.01); *C07C 209/68* (2013.01); *C07C 211/63* (2013.01); *C11D 11/0047* (2013.01); *H01L 21/02057* (2013.01)

(58) Field of Classification Search
CPC ........................... C07C 41/06; C11D 11/0047
(Continued)

(56) References Cited

U.S. PATENT DOCUMENTS 2,256,958 A    9/1941  Muskat
6,776,919 B2   8/2004  Fukunaga et al.
(Continued)

FOREIGN PATENT DOCUMENTS

JP    2002161381 A    6/2002
JP    2003119494 A    4/2003
(Continued)

OTHER PUBLICATIONS

Translation of International Preliminary Report on Patentability, dated Nov. 2020.
(Continued)

*Primary Examiner* — Gregory E Webb
(74) *Attorney, Agent, or Firm* — Cahn & Samuels, LLP

(57) ABSTRACT

A method for producing a quaternary alkylammonium hypochlorite solution includes a preparation step of preparing a quaternary alkylammonium hydroxide solution, and a reaction step of bringing the quaternary alkylammonium hydroxide solution into contact with chlorine, wherein a carbon dioxide concentration in a gas phase portion in the reaction step is 100 ppm by volume or less, and pH of a liquid phase portion in the reaction step is 10.5 or more.

18 Claims, 2 Drawing Sheets

(51) Int. Cl.
  *C07C 209/68* (2006.01)
  *C07C 211/63* (2006.01)
  *C11D 11/00* (2006.01)
  *H01L 21/02* (2006.01)

(58) Field of Classification Search
  USPC .......................................................... 510/175
  See application file for complete search history.

(56) References Cited

U.S. PATENT DOCUMENTS

| 11,390,577 B2 * | 7/2022 | Shimoda ............... C07C 209/68 |
| 2005/0176603 A1 | 8/2005 | Hsu |

FOREIGN PATENT DOCUMENTS

| JP | 2005227749 A | 8/2005 |
| JP | 2009081247 A | 4/2009 |

OTHER PUBLICATIONS

English Abstract for JP2005227749 A, Aug. 25, 2005.
Mohammed et al., "Oxidation of Gem-Chloronitroso- and Vic-Chloronitroso-Alkanes and -Cycloalkanes to Respective Chloronitro Compounds by Novel Cetyltrimethylammonium Hypochlorite Reagent," Journal of Chemical Sciences vol. 123, No. 4, 433-41, 2011.
International Search Report for Application No. PCT/JP2019/019898, dated Aug. 13, 2019.
English Abstract of JP2002161381 A, Jun. 4, 2002.
English Abstract of JP2009081247 A, Apr. 16, 2009.
English Abstract of JP2003119494 A, Apr. 23, 2003.

* cited by examiner

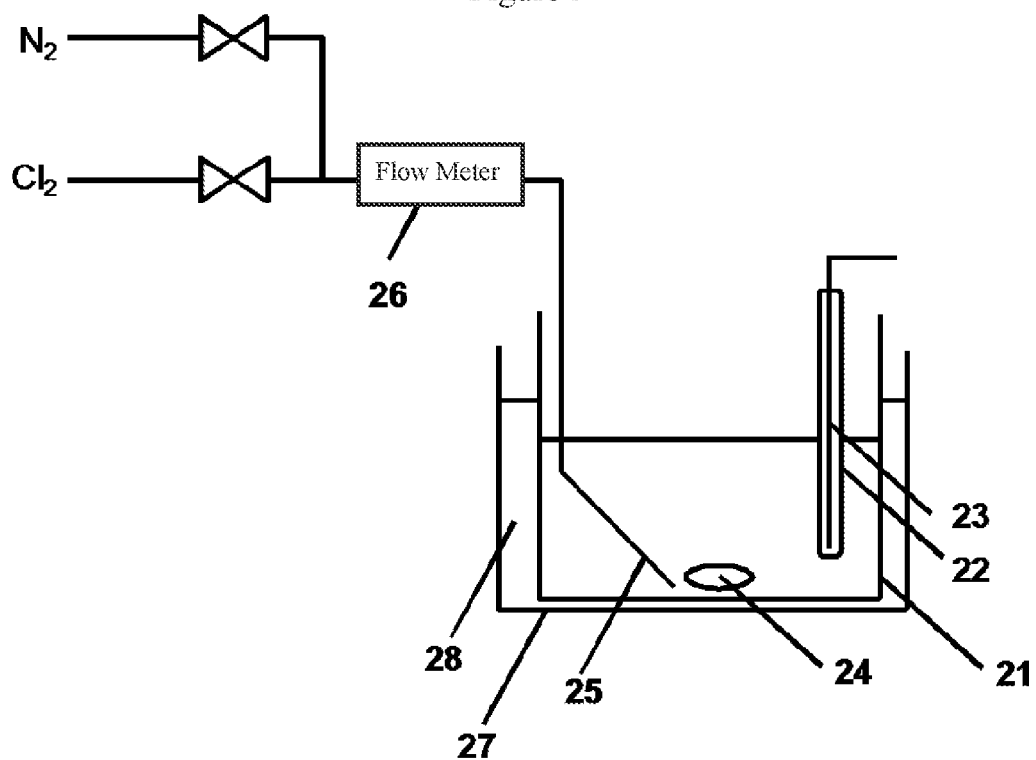

QUATERNARY ALKYLAMMONIUM HYPOCHLORITE SOLUTION, METHOD FOR MANUFACTURING SAME, AND METHOD FOR CLEANING SEMICONDUCTOR WAFER

This application is a U.S. national stage application of PCT/JP2019/019898 filed on 20 May 2019 and claims priority to Japanese patent documents JP 2018-09923 filed on 23 May 2018, JP 2018-099224 filed on 23 May 2018, and JP 2018-116832 filed on 20 Jun. 2018, the entireties of which are incorporated herein by reference.

TECHNICAL FIELD

The present invention relates to a quaternary alkylammonium hypochlorite solution and a method for producing the same. More particularly, the present invention relates to a quaternary alkylammonium hypochlorite solution having excellent storage stability and a method for producing the same. Moreover, the present invention relates to a quaternary alkylammonium hypochlorite solution suitable for cleaning semiconductor wafers and elements and having been reduced in metal impurities, and a method for producing the same.

BACKGROUND OF THE INVENTION

In recent years, fining of design rules of semiconductor elements has been promoted, and requirements for impurity control in the semiconductor element production steps have become severer. Since impurities generated in the steps of producing semiconductor elements differ for each step, it is important to specify a contamination source for each step and to control a concentration of an impurity that becomes the contamination source.

In order to improve production efficiency of semiconductor elements, a large-diameter semiconductor wafer having a diameter of more than 300 mm has been used. In the large-diameter semiconductor wafer, an area of an edge face part or a back face part where electronic devices are not formed is large as compared with that of a small-diameter semiconductor wafer. On that account, in the step of forming metal wiring and the step of forming a barrier metal, a metal wiring material and a barrier metal material (sometimes also referred to as "metal materials" collectively hereinafter) easily adhere to not only a semiconductor wafer front face part where a semiconductor element is formed but also the edge face part and the back face part. As a result, in the large-diameter semiconductor wafer, the amount of extra metal materials adhering to the edge face part and the back face part increases as compared with that in the small-diameter wafer.

The extra metal materials adhered to the edge face part or the back face part of the semiconductor wafer contaminate the inside of the production device as particles of a metal or a metal oxide in an ashing step using oxygen or a dry etching step using plasma, each step being a step after the formation of metal wiring or barrier metal, and they become a cause of cross contamination. On that account, the metal materials adhered to the edge face part or the back face part need to be removed before they are brought in the next step.

Among these metal materials, noble metals typically platinum and ruthenium are not easily oxidized, dissolved and removed in the subsequent etching step or cleaning step. Therefore, it is preferable to remove these noble metals in preference to other metal materials from the semiconductor wafer. In particular, ruthenium is frequently used as a wiring material in a semiconductor element of design rule of 10 nm or less since the resistance value can be decreased more than the case of using copper as a wiring material, and therefore, ruthenium is desired to be rapidly removed from unnecessary parts.

In general, a cleaning method utilizing a hypochlorite having high oxidizability as a cleaning liquid for semiconductor wafers has been proposed. Specifically, a method using a sodium hypochlorite aqueous solution has been proposed (see Patent Documents 1 and 2).

However, in the method using a sodium hypochlorite aqueous solution as a cleaning liquid, sodium ions contained in the cleaning liquid inevitably increase. As a result, sodium ions tend to adhere to the semiconductor wafer, etc., and there is a fear of a decrease in production efficiency of semiconductors.

In contrast with this, development of a cleaning liquid using a hypochlorous acid not containing sodium as an essential component (see Patent Document 3) or a quaternary alkylammonium hypochlorite aqueous solution (see Patent Document 4) has been also carried out.

However, the cleaning liquid using hypochlorous acid (see Patent Document 3) is used for cleaning a substrate having a metal film or a metal oxide film, and does not aim particularly at removal of noble metals. On that account, this liquid is not suitable for cleaning a metal/metal oxide film of a noble metal.

On the other hand, the cleaning liquid containing a tetramethylammonium hypochlorite aqueous solution described in Patent Document 4 is also used for cleaning photoresist and residues, and a copper or aluminum metal coating containing ruthenium is not a cleaning object of this liquid. Specifically, it is shown in the working example that the metal film is hard to etch.

CITATION LIST

Patent Document
Patent Document 1: Japanese Unexamined Patent Application Publication No. 2002-161381
Patent Document 2: Japanese Unexamined Patent Application Publication No. 2009-081247
Patent Document 3: Japanese Unexamined Patent Application Publication No. 2003-119494
Patent Document 4: Japanese Unexamined Patent Application Publication No. 2005-227749

The tetramethylammonium hydroxide solution of Patent Document 4 is not always satisfactory in its storage stability. That is to say, it has found by the studies of the present inventors that because of a decrease of hypochlorite ions exerting oxidative effect with time, desired cleaning performance is not exhibited.

In Patent Document 4, further, it is disclosed that, for example, triazole, thiazole, tetrazole and imidazole are added to a cleaning composition as stabilizers in order to maintain the level of an active halogen.

However, by adding the stabilizers, they are liable to remain as organic residues after cleaning, and they bring about a decrease of yield of semiconductor element. Moreover, the stabilizers are each easily adsorbed on a specific metal, for example, triazole is easily adsorbed on copper, and this sometimes decreases the ability to clean copper.

Accordingly, it is a first object of the present invention to provide a method for producing a quaternary alkylammonium hypochlorite solution which has small change of a hypochlorite ion concentration with time and is excellent in storage stability even if a stabilizer is not added.

The cleaning liquid containing a tetramethylammonium hypochlorite aqueous solution described in Patent Document 4 aims at removal of photoresist and residues, as described above. On this account, reduction of contents of metals in the cleaning liquid, such as sodium, aluminum and/or potassium, has not been taken into consideration. It is thought that as the metal contents in the cleaning liquid decrease, the production efficiency of a semiconductor element can be improved.

Accordingly, it is a second object of the present invention to provide a quaternary alkylammonium hypochlorite solution which is used in the steps of producing a semiconductor element and has been reduced in metal content, and a method for producing the same.

SUMMARY OF THE INVENTION

In order to achieve the first object, the present inventors have earnestly studied. Then, they have found that since pH of a quaternary alkylammonium hypochlorite solution during the reaction is not controlled, the concentration of hypochlorite ions present in the quaternary alkylammonium hypochlorite solution lowers, and the cleaning/removing power decreases.

That is to say, the hypochlorite ion concentration greatly varies depending upon pH of the quaternary alkylammonium hypochlorite solution in the reaction step. Then, the present inventors have further studied variation factors of pH in the reaction step, and as result, they have found that carbon dioxide in the gas phase portion in the reaction step is adsorbed by the reaction solution, and pH of the reaction solution greatly varies, so that by controlling the carbon dioxide concentration in the gas phase portion in the reaction step, a quaternary alkylammonium hypochlorite solution having high storage stability can be produced even if a stabilizer is not added.

On the basis of the above knowledge, the present inventors have furthermore continuously studied, and as a result, they have found that even if a stabilizer is not added, a quaternary alkylammonium hypochlorite solution which can be preferably used as an antioxidant or a cleaning agent is further improved in the storage stability by controlling pH of the quaternary alkylammonium hypochlorite solution.

That is to say, it has been proved that reaction rate of the disproportionation reaction of hypochlorous acid and hypochlorite ion varies depending upon pH of the quaternary alkylammonium hypochlorite solution, and there is a range of pH where self-decomposition of hypochlorous acid and hypochlorite ion is suppressed. It is generally known that when a sodium hypochlorite solution is alkaline, for example, when it has pH of 11 or more, the disproportionation reaction of hypochlorous acid and hypochlorite ion is suppressed, but in the case of a quaternary alkylammonium hypochlorite solution, it has been proved that the disproportionation reaction of hypochlorous acid and hypochlorite ion is specifically suppressed when pH is 12 or more and less than 14.

For example, in the case where the quaternary alkylammonium hypochlorite solution of the present invention is used for cleaning and removing metals, an optimum pH of the quaternary alkylammonium hypochlorite solution is more than 7 and less than 12, but it has been proved by the studies of the present inventor that when the quaternary alkylammonium hypochlorite solution is prepared and stored at pH in such range, its oxidizability is markedly lost in a short time.

From these knowledge, the present inventors have found that by controlling pH of the quaternary alkylammonium hypochlorite solution, the hypochlorite ion concentration is not lowered, and storage stability of the quaternary alkylammonium hypochlorite solution is improved even if a stabilizer is not added.

In order to achieve the second object, the present inventors have furthermore studied. First, they have earnestly studied metal impurities which may be contained in the quaternary alkylammonium hypochlorite solution described in Patent Document 4.

In Patent Document 4, the object is to remove a photoresist, and therefore, the necessity of reducing metal atoms contained in the quaternary alkylammonium hypochlorite solution is not taken into consideration.

Specifically, in the working example of Patent Document 4, a tetramethylammonium hydroxide aqueous solution is allowed to react with chlorine gas in an Erlenmeyer flask to produce a tetramethylammonium hypochlorite aqueous solution. The flask is highly probably a glass container because nothing is noted. According to the present inventors, it has been found in reproducing test of the working example that metal atoms such as sodium are included in relatively large amounts in the resulting quaternary alkylammonium hypochlorite solution.

On that account, the present inventors have studied sources of inclusion of metal atoms such as sodium. It is thought that one of the sources is quaternary alkylammonium hydroxide as a raw material, and a material of the flask. That is to say, since the quaternary alkylammonium hydroxide shows high alkalinity, when it contacts with flask, metal atoms such as sodium dissolve out from the glass that is a material of the flask. Then, the present inventors have found that by suitably selecting the material of the reaction vessel when the quaternary alkylammonium hydroxide aqueous solution is allowed to react with chlorine gas, the above problem can be solved.

That is to say, the present invention includes the following gist.

(1) A method for producing a quaternary alkylammonium hypochlorite solution, comprising:

a preparation step of preparing a quaternary alkylammonium hydroxide solution; and a reaction step of bringing the quaternary alkylammonium hydroxide solution into contact with chlorine; wherein a carbon dioxide concentration in a gas phase portion in the reaction step is 100 ppm by volume or less, and pH of a liquid phase portion in the reaction step is 10.5 or more.

(2) The method according to (1), wherein the quaternary alkylammonium hydroxide solution prepared in the preparation step is a solution of quaternary alkylammonium hydroxide, in which the number of carbon atoms of an alkyl group of the quaternary alkylammonium hydroxide is 1 to 10.

(3) The method according to (1) or (2), wherein in the reaction step, a reaction temperature is −35° C. or higher and 15° C. or lower.

(4) The method according to any one of (1) to (3), wherein in the reaction step, a carbon dioxide concentration in the quaternary alkylammonium hydroxide solution is 500 ppm or less.

(5) A method for producing a quaternary alkylammonium hypochlorite solution, comprising a reaction step of bringing a quaternary alkylammonium hydroxide solution into contact with chlorine gas in a reaction vessel, wherein an inner surface of the reaction vessel, that contacts with the quaternary alkylammonium hydroxide solution is formed of an organic polymer material.

(6) The method according to (5), wherein the organic polymer material is a fluororesin.

(7) The method according to (5) or (6), wherein a water content in the chlorine gas is 10 ppm by volume or less.

(8) The method according to any one of (1) to (7), further comprising a step of filtering a quaternary alkylammonium hypochlorite solution obtained in the reaction step.

(9) The method according to (8), wherein pH of the quaternary alkylammonium hypochlorite solution at 25° C., the solution being to be filtered, is 13.5 or less.

(10) The method according to (9), wherein pH of the quaternary alkylammonium hypochlorite solution at 25° C., the solution being to be filtered, is 12.5 or less.

(11) The method according to any one of (1) to (10), comprising a storage step of storing a reaction solution after the reaction step, wherein in the storage step, pH of the quaternary alkylammonium hypochlorite solution at 25° C. is adjusted to 12.0 or more and less than 14.0.

(12) The method according to (11), comprising a dilution step of adjusting pH of the reaction solution after the storage step, wherein in the dilution step, pH of the quaternary alkylammonium hypochlorite solution at 25° C. is adjusted to 8.0 or more and less than 12.0.

(13) The method according to (12), wherein the dilution step is a step of diluting the stored quaternary alkylammonium hypochlorite solution with a solution having pH of more than 0 and 7 or less at 25° C.

(14) A processing method for a semiconductor wafer, comprising processing a semiconductor wafer surface by the quaternary alkylammonium hypochlorite solution obtained by the method according to any one of (1) to (13).

(15) The processing method according to (14), wherein the semiconductor wafer contains at least one selected from the group consisting of copper, tungsten, tantalum, titanium, cobalt, ruthenium, manganese, aluminum, silicon, silicon oxide, and compounds thereof.

(16) A quaternary alkylammonium hypochlorite solution, wherein a content of each metal of sodium, potassium and aluminum is less than 1 ppb.

(17) The quaternary alkylammonium hypochlorite solution according to (16), wherein, a content of each metal of magnesium, iron, nickel, copper, silver, cadmium and lead is less than 1 ppb.

(18) The quaternary alkylammonium hypochlorite solution according to (16) or (17), having pH of 9.0 or more and 12.5 or less at 23° C.

According to a first embodiment of the present invention of the above (1) to (4), a quaternary alkylammonium hypochlorite solution having high storage stability can be obtained even if stabilizers such as triazole, thiazole, tetrazole and imidazole are not added. Moreover, there is no need to add stabilizers that do not contribute to the cleaning ability to the resulting quaternary alkylammonium hypochlorite solution. Accordingly, when the quaternary alkylammonium hypochlorite solution produced by the present invention is used in the semiconductor production steps, it can be preferably used as a cleaning liquid causing no decrease in yield.

According to a second embodiment of the present invention of the above (5) to (7), a quaternary alkylammonium hypochlorite solution having low metal contents can be obtained. On that account, the quaternary alkylammonium hypochlorite solution can be preferably utilized as an etching solution or a cleaning liquid used for producing a semiconductor element.

Furthermore, since the filtration step of the above (8) to (10) is included, the metal contents in the quaternary alkylammonium hypochlorite solution can be further decreased.

By controlling pH during storage as in the above (11), the storage stability can be further improved.

The effect exerted by each embodiment of the present invention will be more specifically described in detail hereinafter.

BRIEF DESCRIPTION OF DRAWINGS

FIG. 3 is a schematic view showing one mode of a general method for producing a quaternary alkylammonium hypochlorite solution.

DETAILED DESCRIPTION OF THE INVENTION

Figure 1:
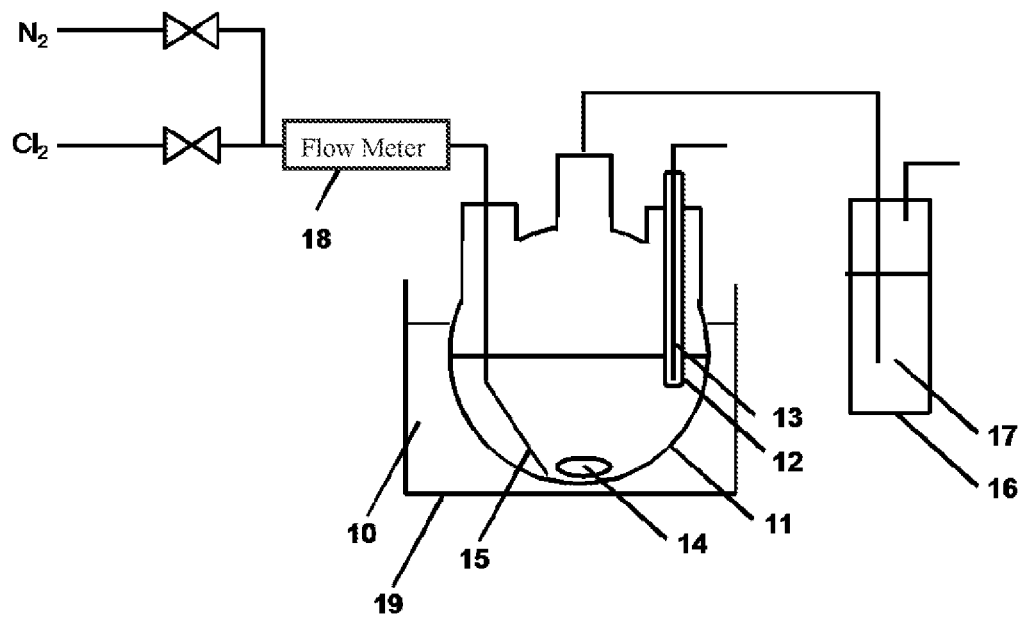
FIG. 1 is a schematic view showing one mode of the method for producing a quaternary alkylammonium hypochlorite solution according to the first embodiment.

First Embodiment: Method for Producing Quaternary Alkylammonium Hypochlorite Solution The method for producing a quaternary alkylammonium hypochlorite solution according to the first embodiment comprises:

a preparation step of preparing a quaternary alkylammonium hydroxide solution; and a reaction step of bringing the quaternary alkylammonium hydroxide solution into contact with chlorine; and is characterized in that:

a carbon dioxide concentration in a gas phase portion in the reaction step is 100 ppm by volume or less, and pH of a liquid phase portion in the reaction step is 10.5 or more.

Each of the steps will be described hereinafter.

(Preparation Step of Quaternary Alkylammonium Hydroxide Solution)

The quaternary alkylammonium hydroxide solution may be any of an aqueous solution in which quaternary alkylammonium hydroxide is dissolved in water and a solution in which quaternary alkylammonium hydroxide is dissolved in a nonaqueous solvent. The quaternary alkylammonium hydroxide solution can be obtained by dissolving quaternary alkylammonium hydroxide in water or a nonaqueous solvent, or diluting a commercial quaternary alkylammonium hydroxide solution to a desired concentration. Examples of the nonaqueous solvents include known organic solvents capable of dissolving quaternary alkylammonium hydroxide. Specific examples thereof include alcohols and glycols, and particularly, methanol and propylene glycol are preferable. Among these solvents, water is preferable as the solvent from the viewpoints of ease of industrially obtaining and availability of a high-purity quaternary alkylammonium hydroxide solution.

The concentration of the quaternary alkylammonium hydroxide solution is not particularly limited, but if the concentration of quaternary alkylammonium hydroxide is high, a salt is precipitated and becomes a solid. Therefore, the concentration of the quaternary alkylammonium hydroxide solution is preferably 0.01 to 30 mass %, more preferably 0.05 to 27.5 mass %, and still more preferably 0.1 to 25 mass %.

In the quaternary alkylammonium hydroxide solution to be prepared, carbon dioxide derived from the atmosphere is usually contained. Carbon dioxide is present in the solution as carbonate ion or bicarbonate ion. Although the carbon dioxide concentration is not particularly restricted, it is preferably 0.001 ppm or more and 500 ppm or less (by mass), more preferably 0.005 ppm or more and 300 ppm or less, and still more preferably 0.01 ppm or more and 100 ppm or less, in terms of carbonate ion. When the concentration of carbon dioxide contained in the quaternary alkylammonium hydroxide solution is 0.001 ppm or more and 500 ppm or less, a change of pH of the resulting quaternary alkylammonium hypochlorite solution can be suppressed. As a result, storage stability of the quaternary alkylammonium hypochlorite solution can be improved. As the quaternary alkylammonium hydroxide solution having such a carbon dioxide concentration, a commercially available one can be utilized.

As the solvent for preparing the quaternary alkylammonium hydroxide solution, only water may be used to prepare an aqueous solution, or an organic solvent may be mixed to prepare a nonaqueous solution. The solvent may be appropriately changed correspondingly to the use purpose of the quaternary alkylammonium hypochlorite solution or the cleaning object. For example, when the cleaning object is ruthenium, sufficient cleaning can be carried out by using only water as the solvent, so that the solution can be prepared as a quaternary alkylammonium hydroxide aqueous solution.

In the present embodiment, the quaternary alkylammonium hydroxide solution is preferably a solution of quaternary alkylammonium hydroxide in which the number of carbons of an alkyl group is 1 to 10, and is more preferably a solution of quaternary alkylammonium hydroxide in which the number of carbons thereof is 1 to 5. Specific examples of the quaternary alkylammonium hydroxides include tetramethylammonium hydroxide, tetraethylammonium hydroxide and tetrabutylammonium hydroxide. These quaternary alkylammonium hydroxides may be used singly or may be used in combination of two or more. The numbers of carbons of four alkyl groups contained in the quaternary alkylammonium hydroxide may be the same as one another or may be different from one another.

In the step of allowing the quaternary alkylammonium hydroxide solution to react with chlorine gas to produce a quaternary alkylammonium hypochlorite solution, pH of the solution containing the quaternary alkylammonium hypochlorite solution produced in the reaction vessel decreases. In the present embodiment, the lower limit of pH of the quaternary alkylammonium hydroxide solution that is the raw material is 10.5 or more, preferably 11.0 or more, still more preferably 11.5 or more, and particularly preferably more than 12.0, taking into consideration the conditions of filtration operation described later and the solubility of quaternary alkylammonium hydroxide. The upper limit of pH of the quaternary alkylammonium hydroxide solution is determined by the concentration of the quaternary alkylammonium hydroxide.

In the quaternary alkylammonium hydroxide solution for use in the present embodiment, the contents of metals, specifically sodium, potassium, aluminum, magnesium, iron, nickel, copper, silver, cadmium and lead, are each preferably 0.01 ppb or more and 20 ppb or less. As a matter of course, the content of a metal contained in the quaternary alkylammonium hydroxide solution used may be less than 0.01 ppb, but it is difficult to obtain such quaternary alkylammonium hydroxide solution.

Therefore, by using a quaternary alkylammonium hydroxide solution having each of the metal contents satisfying the above range, the solution itself is easily available, and removal or reduction of the metal impurities is facilitated by filtration operations during the production of the quaternary alkylammonium hypochlorite solution and after the production thereof. The reason why the metal impurities can be efficiently removed or reduced by the filtration operation is not clear, but it is thought that owing to the presence of certain amounts of metal impurities, not colloids that are difficult to remove by filtration but impurity particles having sizes of a certain degree are formed, and removal by filtration becomes feasible. On that account, owing to lowering of pH of the solution, solids of the metal impurities can be removed or reduced by the filtration operation, and therefore, even a quaternary alkylammonium hydroxide solution that is not an ultrahigh-purity quaternary alkylammonium hydroxide solution can be preferably used. For further enhancing this effect and thereby further removing or reducing impurities that are in the state of ions, particularly at an alkaline region, the contents of metals of sodium, potassium, aluminum, magnesium, iron, nickel, copper, silver, cadmium and lead are each preferably 0.01 ppb or more and 5 ppb or less, and more preferably 0.01 ppb or more and 2 ppb or less.

As such a quaternary alkylammonium hydroxide solution as above, a commercially available one can be used. Among such solutions, a quaternary alkylammonium hydroxide solution that has been made highly pure by an electrolytic method and/or the contact with an ion-exchange resin or the like and is used as a photoresist developing solution for a semiconductor element can be preferably utilized. Such a commercially available one may be used after diluted with a solvent containing no metal impurities, such as ultrapure water.

(Reaction Step of Bringing Quaternary Alkylammonium Hydroxide Solution into Contact with Chlorine)

By the contact and reaction of the quaternary alkylammonium hydroxide solution with chlorine, a hydroxide ion of quaternary alkylammonium hydroxide is replaced with a hypochlorite ion generated by chlorine, and a quaternary alkylammonium hypochlorite solution is produced.

In the present embodiment, chlorine gas is not particularly restricted, and a commercially available one can be adopted. Among them, such a high-purity gas as used for etching of a semiconductor material or as a raw material of a semiconductor material can be used.

Among high-purity gases, one having low water content is particularly preferable, and specifically, one having a water content of 10 ppm by volume or less is preferably used. The reason for this is not clear, but the following can be thought. For example, when a quaternary alkylammonium hypochlorite solution is produced, chlorine gas is usually transported through a pipe. On that account, it is thought that if water is present in a large amount, hydrogen chloride is generated and corrodes the pipe and metal members such as a flowmeter, and the corroded metal impurities are easily introduced into the system together with chlorine gas. Therefore, it is preferable to use chlorine gas having a water content of 10 ppm by volume or less. As a matter of course, commercially available chlorine gas may be used as it is, or immediately before introduction into the reaction system, the water content in chlorine gas can be decreased by bringing a desiccant or the like into contact with the gas. The lower limit of the water content in the chlorine gas is not restricted, but taking industrial availability into consideration, it is 0.1 ppm by volume.

In the present embodiment, the concentration of carbon dioxide contained in the chlorine gas is not particularly restricted, but it is preferably 0.001 ppm by volume or more and 80 ppm by volume or less, more preferably 0.005 ppm by volume or more and 50 ppm by volume or less, and still more preferably 0.01 ppm by volume or more and 2 ppm by volume or less. When the concentration of carbon dioxide contained in the chlorine gas is in the range of 0.001 ppm by volume or more and 80 ppm by volume or less, a change of pH of the resulting quaternary alkylammonium hypochlorite solution can be suppressed. As a result, storage stability of the quaternary alkylammonium hypochlorite solution can be improved. As chlorine gas having such a carbon dioxide concentration, a commercially available one can be utilized.

In the present embodiment, the method for bringing the quaternary alkylammonium hydroxide solution into contact with chlorine is not particularly restricted, and a known method can be adopted. However, in order to avoid inclusion of carbon dioxide into the reaction system, the reaction is preferably carried out in a closed system. As a simplified method, by blowing chlorine into the quaternary alkylammonium hydroxide solution in a three-neck flask as shown in FIG. 1, the reaction can be sufficiently carried out, and a quaternary alkylammonium hypochlorite solution having excellent storage stability can be produced. Alternatively, a reaction device having a structure shown in FIG. 2 may be used though the details will be described later.

In the present embodiment, the amount of the chlorine gas used (total amount of chlorine gas used) is not particularly restructured, but it is preferably 10 to 31000 mL at 0° C. and 1 atm based on 1 liter of the quaternary alkylammonium hydroxide solution. By using chlorine gas in an amount of this range, an abrupt change of pH in the reaction system is suppressed, and removal or reduction of metal impurities by filtration operation becomes easy. The amount of chlorine used based on 1 liter of the quaternary alkylammonium hydroxide solution at 0° C. and 1 atm can also be set to more than 31000 mL, but the extent of lowering or variation of pH of the quaternary alkylammonium hydroxide solution increases, and moreover, unreacted chlorine gas tends to remain. On the other hand, in the case of less than 10 mL, there is a tendency that sufficient hypochlorite ions cannot be generated. Therefore, taking industrial production into consideration, the amount of chlorine gas is preferably in the range of 10 to 31000 mL at 0° C. and 1 atm. Alternatively, the amount of chlorine gas can also be determined by pH of the resulting solution, namely pH of the resulting quaternary alkylammonium hypochlorite solution.

It is preferable to feed chlorine gas into the reaction system at the following rate. From the viewpoints of preventing abrupt lowering of pH and reducing the unreacted chlorine gas, the feed rate (velocity) of the chlorine gas is preferably 0.0034 Pa·m³/sec or more and 16.9 Pa·m³/sec or less at 0° C. and 1 atm based on 1 liter of the quaternary alkylammonium hydroxide solution. Since the feed rate satisfies this range, the reactivity is sufficient, and a quaternary alkylammonium hypochlorite solution can be produced without abrupt lowering or variation of pH. For further exerting this effect, the feed rate of the chlorine gas into the reaction system is more preferably 0.017 Pa·m³/sec or more and 5.1 Pa·m³/sec or less, and still more preferably 0.034 Pa·m³/sec or more and 1.7 Pa·m³/sec or less.

(Gas Phase Portion in Reaction Step)

The most characteristic feature of the present embodiment is that the carbon dioxide concentration in the gas phase portion in the reaction step is 100 ppm by volume or less. In the present embodiment, the gas phase portion is a portion occupied by a gas that comes into contact with the quaternary alkylammonium hydroxide solution, and is, for example, a portion (upper space) occupied by a gas in the three-neck flask 11 in the case of the production method shown in FIG. 1.

In the present embodiment, the upper limit of the carbon dioxide concentration in the gas phase portion is 100 ppm by volume. In the case of a carbon dioxide concentration of more than 100 ppm by volume, carbonate ions and bicarbonate ions are generated by the reactions of the formulae (1) and (2) in the reaction step, and with this, pH of the quaternary alkylammonium hypochlorite solution is lowered.

$$CO_2 + OH^- \rightarrow HCO_3^- \qquad (1)$$

$$HCO_3^- + OH^- \rightarrow CO_3^{2-} + H_2O \qquad (2)$$

It is presumed that if pH is lowered by the above chemical reactions, the hypochlorite ions are decomposed during storage of the resulting quaternary alkylammonium hypochlorite solution, and storage stability is deteriorated.

When the carbon dioxide concentration in the gas phase portion in the present embodiment is 0.001 to 100 ppm by volume, preferably 0.01 to 80 ppm by volume, it becomes possible to sufficiently control pH of the quaternary alkylammonium hypochlorite solution, and a quaternary alkylammonium hypochlorite solution having excellent storage stability can be produced.

(pH in Reaction Step)

The range of pH of the liquid phase portion in the reaction step of the present embodiment is 10.5 or more. The upper limit is not particularly limited, but if pH during the reaction is excessively high and if the solution is stored for a long time at the same pH after completion of the reaction, the hypochlorite ions are decomposed, and the active chlorine concentration sometimes lowers. Therefore, the pH of the liquid phase portion in the reaction step is preferably less than 14, more preferably less than 13.9, and still more preferably 11 or more and less than 13.8. If the pH is in the above range, decomposition of the hypochlorite ions is suppressed during storage of the resulting quaternary alkylammonium hypochlorite solution, and the storage stability is improved. Even if the pH during the reaction is high, the storage stability is improved by controlling pH during storage to a specific range, as described later. On the other hand, if the pH in the reaction step is too low, the storage stability is decreased because of the chemical reaction shown by the formula (3).

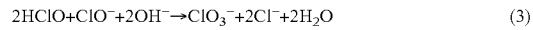

$$2HClO + ClO^- + 2OH^- \rightarrow ClO_3^- + 2Cl^- + 2H_2O \qquad (3)$$

(Reaction Temperature in Reaction Step)

The range of the reaction temperature of the quaternary alkylammonium hydroxide solution in the reaction step of the present embodiment is preferably −35° C. or higher and 15° C. or lower, more preferably −15° C. or higher and 15° C. or lower, and still more preferably 0° C. or higher and 15° C. or lower. If the reaction temperature is in the above range, the quaternary alkylammonium hydroxide solution and chlorine sufficiently react with each other, and a quaternary alkylammonium hypochlorite solution can be obtained with high production efficiency.

When the reaction temperature is lower than −35° C., solidification of the quaternary alkylammonium hydroxide solution begins, and the reaction with chlorine becomes insufficient. On the other hand, when the reaction temperature exceeds 15° C., hypochlorite ions generated in the quaternary alkylammonium hydroxide solution are decomposed by heat. Particularly in the case where pH during the reaction is 13.8 or more, hypochlorite ions are markedly decomposed if the reaction temperature is high. The production efficiency of quaternary alkylammonium hypochlorite can be evaluated by a ratio of the number of moles of the hypochlorite ions generated to the number of moles of chlorine molecules fed as a raw material.

According to the production method of the present embodiment, it is possible to produce a quaternary alkylammonium hypochlorite solution which is excellent in storage stability, for example, which can sufficiently keep the cleaning/removing ability even if 10 days have passed after the production.

As is obvious from this, the quaternary alkylammonium hypochlorite solution obtained by the production method of the present embodiment is excellent in storage stability and can be preferably used in the steps of producing a semiconductor element.

Second Embodiment: Method for Producing Quaternary Alkylammonium Hypochlorite Solution The second embodiment relates to a method for producing quaternary alkylammonium hypochlorite solution, comprising a reaction step of bringing a quaternary alkylammonium hydroxide solution into contact with chlorine gas in a reaction vessel, and is characterized in that an inner surface of the reaction vessel, that contacts with the quaternary alkylammonium hydroxide solution coming into contact, is formed of an organic polymer material. Hereinafter, this embodiment will be described.
(Quaternary Alkylammonium Hydroxide Solution and Chlorine Gas)

As the quaternary alkylammonium hydroxide solution and the chlorine gas, those the same as described in the aforesaid first embodiment can be used.
(Reaction Conditions, Organic Polymer Material Used for Inner Surface of Reaction Vessel)

In the present embodiment, the quaternary alkylammonium hydroxide solution and the chlorine gas are brought into contact with each other in the reaction vessel to produce a quaternary alkylammonium hypochlorite solution. In this case, first, a prescribed amount of the quaternary alkylammonium hydroxide solution is introduced into the reaction vessel, and then, the chlorine gas is introduced in such a manner that the chlorine gas comes into contact with the quaternary alkylammonium hydroxide solution.

In the present embodiment, the inner surface of the reaction vessel that contacts with the quaternary alkylammonium hydroxide solution (sometimes also referred to as an "inner surface of reaction vessel" simply hereinafter) is formed from an organic polymer material. According to the studies of the present inventors, if a reaction vessel made of a general-purpose borosilicate glass is used as the reaction vessel, the quaternary alkylammonium hydroxide solution used as a raw material dissolves metal components contained in the glass, such as sodium, potassium and aluminum. This is thought to be attributable to alkalinity of the quaternary alkylammonium hydroxide solution used as a raw material. On that account, by forming the inner surface of the reaction vessel with an organic polymer material, inclusion of impurities containing the above metals (metal impurities) can be reduced.

When an organic solvent is used, it is preferable to allow the reaction device to have an explosion-proof structure in the present embodiment. Therefore, water is preferably used as the solvent of the quaternary alkylammonium hydroxide solution in order to form simple device configuration.

In the present embodiment, examples of the employable organic polymer materials include vinyl chloride-based resins (soft/rigid vinyl chloride resins), nylon-based resins, silicone-based resins, polyolefin-based resins (polyethylene, polypropylene), and fluorine-based resins. Among them, fluorine-based resins are preferably used taking into consideration ease of molding, solvent resistance, little elution of impurities, etc.

The fluororesin is not particularly restricted as long as it is a resin (polymer) containing a fluorine atom, and a known fluororesin can be used. Examples thereof include polytetrafluoroethylene, polychlorotrifluoroethylene. polyvinylidene fluoride, a tetrafluoroethylene-hexafluoropropylene copolymer, a tetrafluoroethylene-perfluoro(alkyl vinyl ether) copolymer, a tetrafluoroethylene-ethylene copolymer, a chlorotrifluoroethylene-ethylene copolymer, and a cyclopolymer of perfluoro(butenyl vinyl ether). Among them, a tetrafluoroethylene-perfluoro(alkyl vinyl ether) copolymer is preferably used taking into consideration availability of the reaction vessel itself, productivity, etc.

Examples of methods for forming the inner surface of the reaction vessel with the organic polymer material in the present embodiment include a method of forming the whole of the reaction vessel from the organic polymer material and a method of coating only the inner surface of the reaction vessel made of glass or stainless steel with the organic polymer material.

In order to prevent elution of metal components from the organic polymer material, the reaction vessel can also be used after it is cleaned. Specifically, it is preferable to sufficiently clean the reaction vessel with an acid such as high-purity nitric acid or hydrochloric acid (e.g., cleaned by immersing it in a solution of an acid concentration of 1 ml/L for 12 hours) and to further clean it with ultrapure water. Moreover, in order to carry out stable reaction, it is preferable to clean the inner surface of the reaction vessel, which is formed of the organic polymer material, by the above method before the quaternary alkylammonium hydroxide solution and chlorine gas are allowed to react with each other.

In the present embodiment, as long as the inner surface of the reaction vessel, that contacts with the quaternary alkylammonium hydroxide solution, is formed of the organic polymer material, other parts may be formed of glass, stainless steel or passivated stainless steel. However, it is preferable to form a stirring bar, etc. from the same organic polymer material, though it is not essential since the influence is small.

In the present embodiment, the quaternary alkylammonium hydroxide solution and chlorine gas only need to be brought into contact with each other in the reaction vessel, but it is preferable to introduce chlorine gas into the quaternary alkylammonium hydroxide solution that is being stirred. In this case, the range of the reaction temperature is not particularly restricted, but it is preferably the same as in the first embodiment.

If carbon dioxide is present in the reaction system, pH of the resulting quaternary alkylammonium hypochlorite solution tends to lower. Therefore, it is preferable that carbon dioxide should not be contained in the reaction system similarly to the first embodiment, taking stable production into consideration. Specifically, it is preferable to use a quaternary alkylammonium hydroxide solution, chlorine gas, etc. which have been reduced in the amount of carbon dioxide. Further, it is preferable to carry out the reaction in the presence of an inert gas (e.g., nitrogen gas) having been reduced in the amount of carbon dioxide. By carrying out the reaction under such conditions, lowering of pH of the resulting quaternary alkylammonium hypochlorite solution can be suppressed, and therefore, storage stability is improved.

(Reaction Device)

Figure 2:
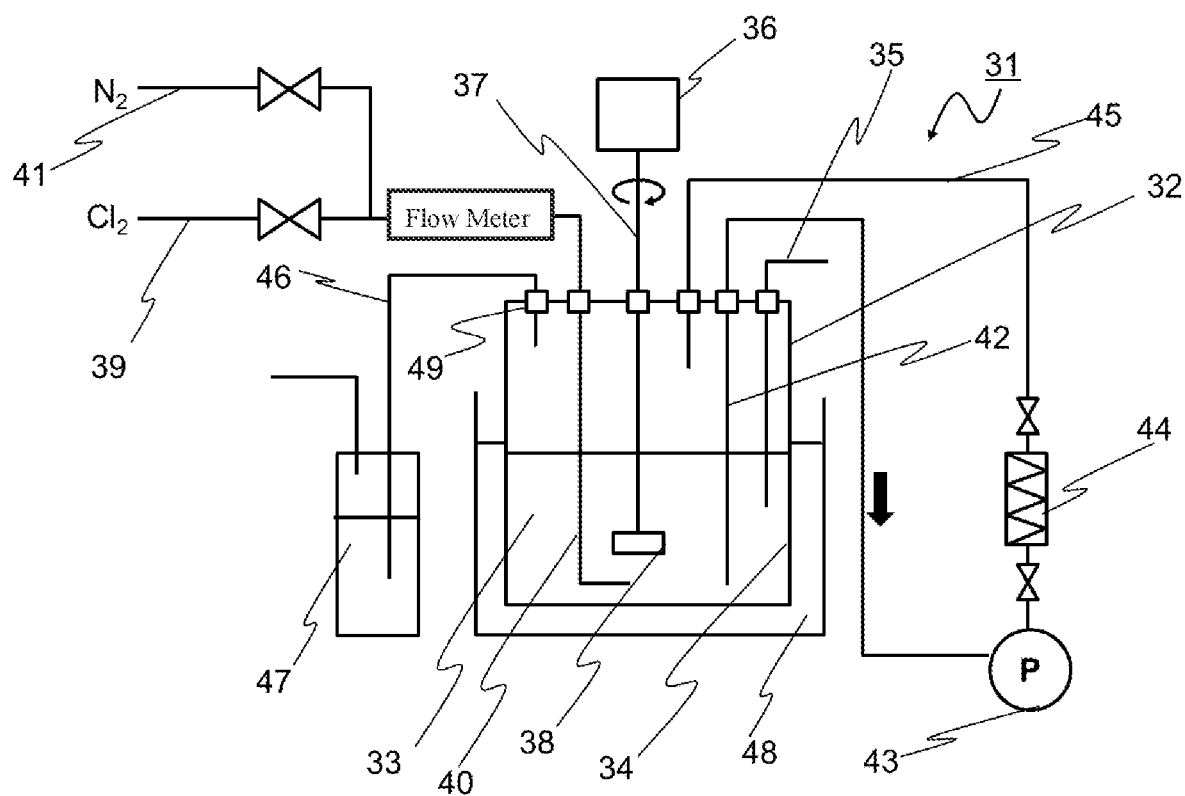
FIG. 2 is a schematic view showing one mode of the method for producing a quaternary alkylammonium hypochlorite solution according to the second embodiment.

Next, the reaction device will be described using one example of a reaction device that can be preferably used in the present embodiment. FIG. 2 is a schematic view of a reaction device 31.

In the reaction device 31, a surface (reaction vessel inner surface) 34 of a reaction vessel 32, that contacts with the quaternary alkylammonium hydroxide solution 33, is formed from the organic polymer material. In this reaction device 31, a thermometer (thermocouple) 35 by which the temperature can be confirmed can also be provided. The reaction device is preferably provided with a stirring motor 36, a stirring bar 37 and a stirring blade 38 so that mixing can be carried out in the reaction system. It is preferable that parts of these thermometer 35, stirring bar 37 and stirring blade 38, which come into contact with the quaternary alkylammonium hydroxide solution 33, be also formed from the organic polymer material.

In the reaction device 31, a chlorine gas feed tube 39 to feed chlorine gas is provided, and through the feed tube 39 and through a gas introduction tube 40 to introduce chlorine gas into the reaction system, the chlorine gas is brought into the vessel so as to contact with the quaternary alkylammonium hydroxide solution 33. As previously described, it is preferable that carbon dioxide should not be contained in the reaction system, and therefore, a nitrogen gas feed tube 41 can also be provided. FIG. 2 shows constitution in which the nitrogen gas feed tube 41 joins the chlorine gas feed tube 39 on its way, and nitrogen gas is introduced through the gas introduction tube 40, but the gas introduction tube 40 may be separated into a chlorine gas introduction tube and a nitrogen gas introduction tube. Since this gas introduction tube 40 contacts with the quaternary alkylammonium hydroxide solution 33, it is preferably formed from the organic polymer material.

In the present embodiment, when the chorine gas and the quaternary alkylammonium hydroxide solution are brought into contact to produce a quaternary alkylammonium hypochlorite solution, pH in the reaction system lowers, and solids containing metal components are sometimes precipitated, as described later in detail. In order to remove or reduce the solids by filtration, a filtration device can also be provided in the present embodiment. This filtration device includes a reaction solution transfer tube 42, a pump 43, a filtration filter 44 and a reaction solution return tube 45. Since these members in the filtration device come into contact with a reaction solution containing quaternary alkylammonium hypochlorite, they are preferably formed from the organic polymer material.

As the pump 43, a chemical diaphragm pump, a tube pump, a magnet pump, or the like can be utilized. Among them, a pump having a liquid contact part formed of the aforesaid fluororesin is preferably used in order to prevent contamination with metal components, and particularly, a magnet pump is preferably used taking availability into consideration.

As the filtration filter 44, one whose material and shape will be described below in detail is preferably used. In FIG. 2, an example of one filtration filter 44 provided is shown, but a plurality of filtration filters 44 can also be provided in series and/or in parallel according to the use purpose (depending on impurities to be removed).

By providing such a filtration device as above, filtration operation can also be carried out in the course of the reaction. Alternatively, by terminating feeding of chlorine gas and by circulating the quaternary alkylammonium hypochlorite solution by the pump 43 after the reaction, solids contained in the solution, which contains metal components, can also be removed or reduced by the filtration filter 44. In FIG. 2, constitution in which the reaction device and the filtration device are integrated with each other is shown, but if filtration is carried out after the reaction, the reaction device and the filtration device may be separately installed.

Furthermore, a chlorine gas exhaust tube 46 to release unreacted chlorine gas, and a chlorine gas trap 47 can also be provided. In the chlorine gas trap 47, a sodium hydroxide aqueous solution of, for example, about 5 mass % is placed.

Around the reaction vessel 32, a reaction bath 48 to control the reaction temperature can also be provided.

The thermometer 35, the stirring bar 37, the gas introduction tube 40, the reaction solution transfer tube 42, the reaction solution return tube 45 and the chlorine gas exhaust tube 46 can be each connected to the reaction vessel 32 by a half joint 49 or the like.

By using such a reaction device 31, the method of the present embodiment can be easily carried out, and a quaternary alkylammonium hypochlorite solution having high purity can be produced.

<Filtration Step>

When a quaternary alkylammonium hypochlorite solution is produced by the contact of the quaternary alkylammonium hydroxide solution with the chlorine gas, pH of the solution in the reaction system lowers. In this reaction, solids containing metal impurities are sometimes precipitated, and in order to remove or reduce the solids, a preferred embodiment includes a step of filtration. That is to say, it is preferable to filter the quaternary alkylammonium hypochlorite solution obtained in the course of the reaction of the first embodiment and the second embodiment or obtained by feeding chlorine gas up to a prescribed concentration. The filtration step may be carried out after the storage step or the dilution step described later.

In the filtration step, metal impurities to be filtered sometimes vary depending upon pH of the quaternary alkylammonium hypochlorite solution.

Specifically, when pH of the quaternary alkylammonium hypochlorite solution is 13.5 or less, preferably, when pH of the solution is more than 12.5 and 13.5 or less, hydroxides of magnesium, iron, cadmium and the like and oxides of nickel and silver are solidified, so that by carrying out filtration operation, these impurities can be also removed or reduced.

When pH of the quaternary alkylammonium hypochlorite solution is 12.5 or less, preferably, when pH of the solution is 9.0 or more and 12.5 or less, oxides of copper and lead are solidified in addition to the above impurities, so that by carrying out filtration operation, these impurities can be also removed or reduced. pH of the solution sometimes varies depending upon the temperature. The above pH uses a value at 25° C. as a standard. When the filtration step is actually carried out, the liquid temperature is not limited to 25° C., and the filtration step is carried out preferably at 20° C. to 28° C., more preferably 23° C. to 25° C.

Solids of such metal impurities are produced even if the purity of the quaternary alkylammonium hydroxide solution and chlorine gas that are raw materials is increased. Even in the case where the inner surface of the reaction vessel is formed from the organic polymer material, the solids are sometimes produced. Although the source of this is not clear, it is presumed that because a highly corrosive chlorine gas is used, metal impurities coming from somewhere in the reaction system are contaminated in the reaction vessel.

The filtration operation is carried out at pH at which metals intended to be removed or reduced are solidified. On that account, the filtration operation may be carried out only once, or may be carried out a plurality of times at each pH. In this case, a plurality of filtration filters different in pore diameter are prepared at each pH, and by performing filtration using the filtration filters in order from a filtration filter of the largest pore diameter, the filtration efficiency is more improved. Specifically, the filtration can be carried out by removing coarse particles in the first stage and by removing fine particles in the second stage. Among solids containing metal components such as impurities of metals, metal oxides, metal hydroxides, and/or colloidal substance, particles of 1 μm or more and 100 μm or less are sometimes referred to as "coarse particles" simply hereinafter. On the other hand, particles of 0.01 μm or more and less than 1 μm are sometimes referred to as "fine particles" simply hereinafter. The particle diameter of a solid refers to an equivalent circle diameter measured by laser diffraction.

The filtration operation is not particularly restricted, and can be carried out using known filtration device and filtration filter. However, in order not to increase unnecessary metal components, it is preferable that a surface of the filtration device, that may contacts with the quaternary alkylammonium hypochlorite solution, be formed of an organic polymer material. As this organic polymer, the same one as previously given as an example can be used.

As a specific filtration filter, a filtration filter made of an organic polymer material or an inorganic material is preferably used. Examples of such filtration filters include filtration filters made of polyolefin (polypropylene, polyethylene, ultrahigh-molecular weight polyethylene), polysulfone, cellulose acetate, polyimide, polystyrene, the aforesaid fluorine-based resin, and/or quartz fiber. For the filtration filter, a membrane positively charged and a membrane negatively charged are preferably used in combination. The reason for this is that many metal oxides and metal hydroxides are negatively charged in an alkaline atmosphere, and it becomes possible for the positively charged filtration filter to effectively remove the metal components by electrostatic adsorption. Parts of metal components are present in the state of cations and are positively charged. On this account, it becomes possible for the negatively charged filtration filter to effectively remove the ionized metal components by electrostatic adsorption.

The pore diameter of the filtration filter is not particularly restricted, but for the removal of coarse particles, a filtration filter having a pore diameter of 1 μm or more or a microfiltration filter can be used. On the other hand, for the removal of fine particles, a microfiltration filter having a pore diameter of 0.01 μm or more and less than 1 μm, an ultrafiltration filter or a nanofiltration membrane can be used.

As such filtration filter, a commercially available one can be used. Specifically, "Fluoroguard ATX filter (pore diameter 0.05 μm)" made of polytetrafluoroethylene, "Quick-Change ATE filter (pore diameter 0.03 μm)", "Torrento ATE filter (pore diameter 0.02 μm)", or "Fluoroline P-1500 (pore diameter 0.05 μm, 0.1 μm)", each being manufactured by Nihon Entegris G.K., can be used.

The above filtration operation can be carried out before pH of the quaternary alkylammonium hypochlorite solution is adjusted to the range suitable for its use purpose. In this case, the filtration operation is once carried out, and thereafter, the filtrate is mixed with chlorine gas again, whereby a quaternary alkylammonium hypochlorite solution having a desired pH can be obtained. Alternatively, by mixing the filtrate with water, an acid such as hydrogen chloride, and/or an alkali such as a quaternary alkylammonium hydroxide solution, a quaternary alkylammonium hypochlorite solution having a desired pH can also be obtained. On the other hand, when pH of the quaternary alkylammonium hypochlorite solution produced is suitable as pH of a cleaning liquid, the solution is filtered, and the filtrate is used as it is as a cleaning liquid for use in the production of a semiconductor element.

By carrying out such filtration operation, metal components, such as magnesium, iron, nickel, copper, silver, cadmium and lead, can be particularly reduced.

<Storage Step>

The quaternary alkylammonium hypochlorite solution after the reaction step in the first and the second embodiments or after the above filtration step can be used for the prescribed purpose such as a cleaning liquid, as it is, but in general, it is used after a storage step (including storage and transportation). A quaternary alkylammonium hypochlorite solution alone is poor in storage stability, and addition of a stabilizer has been needed. However, a stabilizer may cause an organic substance residue, and improvement has been sought. But by storing the quaternary alkylammonium hypochlorite solution as described below, it becomes possible to supply a quaternary alkylammonium hypochlorite solution having been further improved in storage stability.

The method for producing a quaternary alkylammonium hypochlorite solution according to a preferred embodiment of the present invention includes a storage step for storing a reaction solution after the reaction step, and in the storage step, pH of the quaternary alkylammonium hypochlorite solution at 25° C. is adjusted to 12.0 or more and less than 14.0. After the reaction step, the filtration step may be carried out, and thereafter, the storage step may be carried out.

The concentration of the quaternary alkylammonium hypochlorite solution that is a storage object is not particularly restricted, but taking industrial production into consideration, preferable is a quaternary alkylammonium hypochlorite solution containing a hypochlorite ion in an amount of 0.001 to 20 mass % and a quaternary alkylammonium ion in an amount of 0.001 to 50 mass % at a prescribed pH. The "prescribed pH" refers to any pH of 12.0 or more and less than 14.0, which is selected as pH in the storage step.

In addition, various additives may be compounded with the quaternary alkylammonium hypochlorite solution according to the use purpose of the solution, when needed. For example, a metal chelating agent, a complexing agent, a metal dissolution accelerator, a metal corrosion inhibitor, a surfactant, an acid, an alkali, etc. can be added as the additives. By adding these additives, acceleration or inhibition of metal dissolution, improvement of surface roughness, enhancement of processing rate, reduction of particle adhesion, etc. can be expected in the semiconductor wafer processing, so that a cleaning liquid containing these additives is preferably utilized for the semiconductor wafer processing.

In the method for storing the quaternary alkylammonium hypochlorite solution according to a preferred embodiment, the quaternary alkylammonium hypochlorite solution is stored at pH in the limited range. The storage method will be described below in detail.

Here, the "storage" means time period between the time of beginning of storage in the state where pH of the quaternary alkylammonium hypochlorite solution at 25° C. is 12 or more and less than 14 and the time of adjustment of concentration and/or pH of the quaternary alkylammonium hypochlorite solution for the next step. If pH of the solution after the adjustment of pH is 12 or more and less than 14 and if the solution is further stored, this storage also corresponds to the storage of the present invention. If pH of the quaternary alkylammonium hypochlorite solution is 12 or more and less than 14 from the beginning, the solution is stored as it is, and if pH thereof is less than 12 or 14 or more, the solution is stored after pH is adjusted to 12 or more and less than 14.

The pH of the solution sometimes varies depending upon the temperature. The above pH uses a value at 25° C. as a standard. When the solution is actually stored, the liquid temperature is not limited to 25° C. Accordingly, the conditions in the storage are not particularly limited, but the solution is preferably stored under the normal storage conditions, that is, it is preferable to store the solution in a known container such as a canister or a storage container made of a resin at −25 to 50° C., and it is more preferable to store the solution in a storage container capable of light shielding, a transportation container such as a canister, or a storage container made of a resin, each container having been filled with an inert gas, at −20 to 40° C. in a dark place. When the storage temperature exceeds the above range, hypochlorite ions are thermally decomposed during storage for a long time to generate oxygen molecules, whereby the container may expand and break.

In a preferred embodiment, a quaternary alkylammonium hypochlorite solution having pH of 12 or more and less than 14 at 25° C. is stored. If the pH is in this range, the hypochlorite ion concentration does not decrease, and storage for a long time is possible. If the pH is less than 12, the disproportionation reaction of hypochlorite ions proceeds, the hypochlorite ions are decomposed, and the oxidizability of the quaternary alkylammonium hypochlorite solution is decreased. On the other hand, if the pH is 14 or more, it is presumed that organic ions that are cations are decomposed. As a result, it is presumed that the disproportionation reaction of the hypochlorite ions, which has been inhibited by bulkiness of the organic ions, proceeds again, and the hypochlorite ions are decomposed. It is preferable to store the quaternary alkylammonium hypochlorite solution having pH of 12 or more and less than 13.9 at 25° C., and it is more preferable to store the quaternary alkylammonium hypochlorite solution having pH of 12 or more and less than 13.8 at 25° C.

The reason why the storage stability is improved by the above storage method, but the present inventors have presumed as follows. It is presumed that in the quaternary alkylammonium hypochlorite solution, a part of quaternary alkyl ammonium hypochlorite is dissociated into hypochlorite ion and organic ion, but in most of it, hypochlorite ion and organic ion are ionically bonded, and the steric bulkiness of the organic ion suppresses the disproportionation reaction of the hypochlorite ion. It is thought that on this account, as the steric bulkiness of the organic ion increases, the disproportionation reaction is more suppressed, and the storage stability is more improved. If the organic ion is a bulky quaternary alkylammonium ion such as a tetramethylammonium ion, the disproportionation reaction can be sufficiently suppressed.

According to the storage method of the present invention, the oxidizability of the quaternary alkylammonium hypochlorite solution during storage hardly changes even if the storage time is 30 days, preferably 60 days, and more preferably 90 days. Therefore, after the storage, by just diluting the quaternary alkylammonium hypochlorite solution according to the use conditions, the solution can be used for various purposes. As the storage time becomes longer, the effect of improving productivity can be more expected.

(Dilution Step)

The quaternary alkylammonium hypochlorite solution is sometimes used after it is appropriately diluted according to the use purpose. After the quaternary alkylammonium hypochlorite solution is stored at pH of 12 or more during the above storage step, the quaternary alkylammonium hypochlorite solution is diluted with a solution having pH of less than 12 to adjust the pH of the quaternary alkylammonium hypochlorite solution to 8.0 or more and less than 12.0 in the dilution step.

In the method for diluting the quaternary alkylammonium hypochlorite solution, it is sufficient that the concentration of hydrogen ion contained in the quaternary alkylammonium hypochlorite solution can be relatively increased, so that the quaternary alkylammonium hypochlorite solution may be diluted with water, may be diluted with a solution containing an acid, or may be diluted with a solution having pH lower than the pH of the quaternary alkylammonium hypochlorite solution during storage. As an example of the solution having pH lower than the pH of the quaternary alkylammonium hypochlorite solution that has been stored by the storage method of the present invention, an alkaline solution such as a quaternary alkylammonium hydroxide solution having pH of less than 12 can be mentioned.

In the solution that is added to dilute the quaternary alkylammonium hypochlorite solution, quaternary alkylammonium hypochlorite may be contained or may not be contained. For example, when the quaternary alkylammonium hypochlorite solution is diluted with a solution containing quaternary alkylammonium hypochlorite, not only adjusting the pH but also the concentration of the quaternary alkylammonium hypochlorite solution can be arbitrarily adjusted.

In the present invention, the solution added to dilute the quaternary alkylammonium hypochlorite solution is preferably diluted with a solution having pH of more than 0 and 7 or less. By using an acidic solution, the extent of lowering of concentration of the quaternary alkylammonium hypochlorite solution accompanying the pH adjustment can be decreased. Specific examples of the solutions having pH of more than 0 and 7 or less include inorganic acids, such as hydrochloric acid, nitric acid, sulfuric acid, phosphoric acid, boric acid, hydrofluoric acid, bromic acid, chloric acid, perchloric acid, iodic acid, periodic acid and carbonic acid, and organic acids, such as formic acid, acetic acid, glacial acetic acid, propionic acid, citric acid, oxalic acid, malic acid, lactic acid and benzoic acid.

In addition, when the impurity concentration of the solution used for the dilution is high, use purposes of the resulting diluted solution are limited, so that the amount of impurities in the solution used for the dilution is preferably small. For example, when the quaternary alkylammonium hypochlorite solution is used as a processing liquid for a semiconductor wafer, high purity is required, and therefore, it is preferable to dilute the high-purity quaternary alkylammonium hypochlorite solution with hydrochloric acid, sulfuric acid or the like that can be industrially easily and highly purified.

The method for diluting the quaternary alkylammonium hypochlorite solution is not particularly restricted, and the solution is diluted by a known method. For example, a method in which the quaternary alkylammonium hypochlorite solution and a solution used for dilution are fed from respective two feed openings of a container and stirred using a propeller or a rotor to mix them may be used, or a method in which the liquids are circulated by using a pump to mix them may be adopted. Moreover, the quaternary alkylammonium hypochlorite solution may be diluted by feeding the solution for use in the dilution to the container in which the quaternary alkylammonium hypochlorite solution has been stored.

In another dilution method, the quaternary alkylammonium hypochlorite solution and the solution for use in the dilution are mixed at the place where a quaternary alkylammonium hypochlorite solution-containing composition is used, whereby the quaternary alkylammonium hypochlorite solution can also be diluted. For example, by feeding the quaternary alkylammonium hypochlorite solution and the solution for use in the dilution to the point of use from respective two nozzles, dilution can be carried out at the point of use. This method is particularly effective for processing a semiconductor wafer.

In addition, when the diluted solution is used for semiconductor cleaning, such method can be adopted that an inorganic acid or an organic acid is added to the quaternary alkylammonium hypochlorite solution to dilute the solution. There is a method in which a pipe for feeding the quaternary alkylammonium hypochlorite solution and a pipe for feeding an inorganic acid or an organic acid are allowed to join together on the way to mix them, thereby carrying out dilution, and the resulting diluted solution is fed to a semiconductor wafer that is a surface to be cleaned. For this mixing, a known method, such as a method including passing solutions through narrow passages under pressure to allow them to collide with each other and thereby mix them, a method including filling a pipe with a filler such as a glass tube and repeating distribution-separation and joining, or a method including providing a blade that rotates by power in a pipe, can be adopted.

As described above, by adopting a dilution step, it becomes possible to utilize a diluted solution that stably keeps the oxidizability as compared with a case where the quaternary alkylammonium hypochlorite solution is stored at pH at which the solution is used. When the quaternary alkylammonium hypochlorite solution is used as a cleaning liquid or the like, the solution is generally diluted to pH of about 8 to 12, but if the quaternary alkylammonium hypochlorite solution is stored at this pH, the hypochlorite ion concentration lowers, and the cleaning performance is decreased. However, by storing the solution as mentioned in the above storage step and thereafter carrying out the dilution step, a diluted solution (cleaning liquid) having a high hypochlorite ion concentration is obtained.

(Method for Processing Semiconductor Wafer)

The processing method of the present invention is capable of etching, cleaning or removing various metals and their compounds present on a semiconductor wafer without damaging the semiconductor wafer. However, the processing objects are not limited thereto, and as a matter of course, the processing method can be utilized for cleaning a semiconductor wafer having no metals on its surface, or can be used for wet etching of metals, or the like.

The object of the processing method of the present invention is preferably a semiconductor wafer having a compound containing at least one selected from the group consisting of copper, tungsten, tantalum, titanium, cobalt, ruthenium, manganese, aluminum, silicon, silicon oxide, and compounds thereof. The present invention can effectively exert strong oxidative effect of hypochlorite ions, so that the present invention can be preferably used for treating of noble metals that are not easily oxidized among the above metals. Accordingly, the processing method of the present invention can be preferably used in the case where noble metals, particularly ruthenium, is cleaned or removed. For example, in the case where ruthenium is cleaned or removed, a known cleaning method ca n be adopted.

As described above, according to the storage method of the present invention, a quaternary alkylammonium hypochlorite solution capable of sufficiently keeping the cleaning/removing power even if 30 days have passed after the production can be provided. Thus, a quaternary alkylammonium hypochlorite solution having excellent storage stability is provided, and thereby, costs for transportation or storage of the quaternary alkylammonium hypochlorite solution can be reduced, and this is industrially extremely important.

<Quaternary Alkylammonium Hypochlorite Solution>

By the production method of the second embodiment or by further carrying out a filtration step, a quaternary alkylammonium hypochlorite solution having been reduced in the contents of metal components can be produced. As a matter of course, the solvent of the quaternary alkylammonium hypochlorite solution is the same as the solvent of the quaternary alkylammonium hydroxide solution that is a raw material, but other solvents can also be added as long as the effect of the present invention is not hindered. However, taking into consideration operability, ease of handling, versatility, etc., the solvent of the quaternary alkylammonium hypochlorite solution is preferably water.

By the production method of the second embodiment or by further carrying out a filtration step, the contents of metal components, specifically, sodium, potassium and aluminum, in the resulting quaternary alkylammonium hypochlorite solution can be each reduced to less than 1 ppb (by mass). The contents of these metal components are values measured by the inductively coupled plasma mass spectrometry shown in the working example.

By further carrying out the filtration step previously described, the contents of magnesium, iron, nickel, copper, silver, cadmium and lead in the resulting quaternary alkylammonium hypochlorite solution can be each reduced to less than 1 ppb (by mass). The contents of these metal components are also values measured by the inductively coupled plasma mass spectrometry shown in the working example.

On that account, the contents of sodium, potassium, aluminum, magnesium, iron, nickel, copper, silver, cadmium and lead in the quaternary alkylammonium hypochlorite solution are each most preferably less than 1 ppb. The form of each metal component in the quaternary alkylammonium hypochlorite solution is not particularly limited, and each metal component may be contained as a metal atom or an ion, or may be in the form of a fine particle of an oxide or a hydroxide, a complex or the like.

pH of the resulting quaternary alkylammonium hypochlorite solution is not particularly restricted, and the pH is appropriately determined according to the use purpose. For example, when the quaternary alkylammonium hypochlorite solution has pH of more than 12.5, the solution can also be used as a photoresist remover (developing solution), or the solution can also be used for flattening a noble metal layer when a semiconductor element is formed.

Particularly, by setting pH to 9.0 or more and 12.5 or less, the resulting quaternary alkylammonium hypochlorite solution can also be used for etching treatment of noble metals. In this case, the pH can be set to 9.0 or more and 12.5 or less while feeding chlorine gas to a quaternary alkylammonium hydroxide solution having high pH, and therefore, the production is also easy. In addition, by carrying out filtration operation during the production or after the production, it becomes also possible to further reduce the contents of metal components.

In the quaternary alkylammonium hypochlorite solution obtained by the present invention, known additives, such as benzotriazoles, benzophenones, oxanilides and salicylates, which are common stabilizes, can also be compounded. By adding the stabilizers, storage stability is improved.

EXAMPLES

Next, the present invention will be described in detail using examples and comparative examples, but it should be construed that the present invention is in no way limited to the examples. First, the measuring devices used, the production method for each component, etc. will be described.

<pH Measuring Method>

The quaternary alkylammonium hydroxide solution and the quaternary alkylammonium hypochlorite solution in each amount of 30 mL were each subjected to pH measurement using a benchtop pH meter (LAQUA F-73, manufactured by HORIBA, Ltd.). The pH measurement was carried out after the solutions were stabilized at 23° C.

<Calculation Methods for Active Chlorine Concentration and Hypochlorite Ion Concentration>

To a 100 mL Erlenmeyer flask, 0.5 mL of the quaternary alkylammonium hypochlorite solution as a processing liquid, 2 g of potassium iodide (manufactured by FUJIFILM Wako Pure Chemical Corporation, special grade chemical), 8 mL of 10 mass % acetic acid, and 10 mL of ultrapure water were added, and they were stirred until solids were dissolved, thereby obtaining a brown solution.

The prepared brown solution was subjected to oxidation-reduction titration using a 0.02 M sodium thiosulfate solution (manufactured by FUJIFILM Wako Pure Chemical Corporation, for volumetric analysis) until the color of the solution turned to very light yellow from brown, and subsequently, a starch solution was added, thereby obtaining a light purple solution.

To this solution, a 0.02 M sodium thiosulfate solution was further continuously added, and at the time when the resulting solution turned to colorless and transparent, this point is regarded as the end point, and an active chlorine concentration was calculated. From the resulting active chlorine concentration, a hypochlorite ion concentration was calculated. For example, if the active chlorine concentration is 1 mass %, the hypochlorite ion concentration is 0.73 mass %.

<Measurement Method for Carbon Dioxide Concentration in Gas Phase Portion>

A carbon dioxide concentration in the gas phase portion in the reaction solution was measured using a $CO_2$ monitor (manufactured by CUSTOM CORPORATION, $CO_2$-M1).

<Reaction Efficiency>

From a ratio (%) of the number of moles of hypochlorite ions generated to the number of moles of chlorine molecules fed, reaction efficiency was determined. When the total amount of chlorine added has undergone reaction (decomposition has not occurred), the reaction efficiency becomes 100%. When hypochlorite ions are decomposed during the reaction, the reaction efficiency decreases.

<Evaluation Method 1 for Storage Stability>

Into a glove bag, the quaternary alkylammonium hypochlorite solution was transferred, and after the carbon dioxide concentration in the glove bag became 1 ppm or less, the solution was transferred into a container made of PFA, followed by sealing the container. Next, the quaternary alkylammonium hypochlorite solution was stored for 10 days in light-shielded environment at 23° C., and thereafter, the hypochlorite ion concentration in the quaternary alkylammonium hypochlorite solution in the container made of PFA was measured. A hypochlorite ion concentration ratio (concentration after 10 days/initial concentration) of 60% or more and 100% or less was evaluated as good, and a hypochlorite ion concentration of less than 60% was evaluated as poor.

<Evaluation Method 2 for Storage Stability>

Into a glove bag, the quaternary alkylammonium hypochlorite solution was transferred, and after the carbon dioxide concentration in the glove bag became 1 ppm or less, the solution was transferred into a container made of PFA. Next, the quaternary alkylammonium hypochlorite solution was stored for 30 days in light-shielded environment at 23° C., and thereafter, the hypochlorite ion concentration in the quaternary alkylammonium hypochlorite solution in the container made of PFA was measured. A hypochlorous acid residual ratio (hypochlorite ion concentration after 30 days/initial hypochlorite ion concentration) of 50% or more was evaluated as good, and a hypochlorous acid residual ratio of less than 50% was evaluated as poor because a problem of difficulty in practical use might occur.

<Calculation Method for Etching Rate of Ruthenium>

An oxide film was formed on a silicon wafer using a batch type thermal oxidation furnace, and thereon, a ruthenium film of 200 Å (±10%) was formed using a sputtering method. A sheet resistivity was measured by a four-probe resistivity measuring device (Loresta-GP, manufactured by Mitsubishi Chemical Analytech Co., Ltd.), and it was converted into a film thickness. Specifically, 30 ml of the resulting quaternary alkylammonium hypochlorite solution was prepared in a beaker, and when a quaternary alkylammonium hypochlorite solution has pH of more than 12, it was diluted with an inorganic acid or an organic acid so as to have desired pH, thereby obtaining a measurement solution. In this measurement solution, each sample piece obtained by cutting the wafer with ruthenium film into a size of 10×20 mm was immersed for 1 minute, and a value obtained by dividing a change in film thickness between before and after the processing by the immersion time was determined as an etching rate, and this was evaluated as a ruthenium etching rate. It is known that as pH increases, the etching rate decreases. Therefore, the range where practical use was possible at each pH was determined as follows. When pH was 9.1, a ruthenium etching rate of 300 Å/min or more was evaluated as good, and that of less than 300 Å/min was evaluated as poor. When pH was 9.5, a ruthenium etching rate of 100 Å/min or more was evaluated as good, and that of less than 100 Å/min was evaluated as poor. When pH was 10.5, a ruthenium etching rate of 20 Å/min or more was evaluated as good, and that of less than 20 Å/min was evaluated as poor. When pH was 11.0, a ruthenium etching rate of 5 Å/min or more was evaluated as good, and that of less than 5 Å/min was evaluated as poor.

<Measuring Method for Metal Concentrations in Quaternary Alkylammonium Hypochlorite Solution>

For the measurement of metal concentrations in the quaternary alkylammonium hypochlorite solution, high resolution inductively coupled plasma mass spectrometry was used.

To a 25 mL volumetric flask made of polyfluoroalkyl ether (PFA) (manufactured by AS ONE CORPORATION, PFA Volumetric Flask), ultrapure water and 1.25 mL of high-purity nitric acid (manufactured by KANTO CHEMICAL CO., INC., Ultrapure-100 Nitric Acid) were added. Then, using a pipette (manufactured by AS ONE CORPORATION, Pipetman P1000) and a pipette tip made of fluororesin (manufactured by AS ONE CORPORATION, Fluororesin Pipette Tip), 0.25 mL of the quaternary alkylammonium hypochlorite solution was sampled and added to the PFA volumetric flask, followed by stirring. Subsequently, dilution with ultrapure water was carried out to prepare a measurement sample having been diluted 100 times. Further, using a high resolution inductively coupled plasma mass spectrometer (manufactured by ThermoFisher Scientific, Element 2), the amounts of metals were determined by a calibration method. In order to confirm increase or decrease in sensitivity due to matrix, a solution obtained by adding impurities to the measurement solution in such a manner that the impurity content became 2 ppb was also subjected to the measurement. The measurement conditions: RF output was 1500 W, and as argon gas flow rates, a plasma gas flow rate was 15 L/min, an auxiliary gas flow rate was 1.0 L/min, and a nebulizer gas flow rate was 0.7 L/min.

Example 1

<Preparation of Tetramethylammonium Hypochlorite Solution>

In a 2 L three-neck flask made of glass (manufactured by VIDTEC), 253 g of a 25 mass % tetramethylammonium hydroxide (TMAH) aqueous solution having a $CO_2$ content of 2 ppm and 747 g of ion-exchanged water were mixed, thereby obtaining a 6.3 mass % TMAH aqueous solution having a $CO_2$ content of 0.5 ppm. The pH at this time was 13.8. The $CO_2$ concentration in the laboratory was 350 ppm.

Subsequently, as shown in FIG. 1, a rotor 14 (manufactured by AS ONE CORPORATION, total length 30 mm×diameter 8 mm) was placed inside the three-neck flask 11, in one opening of the flask a thermometer protection tube 12 (manufactured by VIDREC, bottom seal type) and a thermocouple 13 were introduced, through another opening thereof a tip of a tube 15 made of PFA (manufactured by FRON INDUSTRY, F-8011-02) which was connected to a chlorine gas container and a nitrogen gas container and capable of arbitrary switching between chlorine gas and nitrogen gas was inserted in the bottom of the solution, and the remaining opening thereof was connected to a gas wash bottle 16 (manufactured by AS ONE CORPORATION, gas wash bottle, model number 2450/500) filled with a 5 mass % sodium hydroxide aqueous solution 17. Next, nitrogen gas having a carbon dioxide concentration of less than 1 ppm was allowed to flow through the tube made of PFA at 0.289 Pa·m$^3$/sec (converted value at 0° C.) for 20 minutes to purge carbon dioxide from the gas phase portion. At this time, the carbon dioxide concentration in the gas phase portion in the flask was 1 ppm or less.

Thereafter, a magnetic stirrer (manufactured by AS ONE CORPORATION, C-MAG HS10) was set at the lower part of the three-neck flask and rotated at 300 rpm to perform stirring, and while cooling the outer periphery of the flask with ice water, chlorine gas (manufactured by Fujiox Co., Ltd., specification purity 99.4%) was fed at 0.064 Pa·m$^3$/sec (converted value at 0° C.) for 180 minutes, thereby obtaining a tetramethylammonium hypochlorite solution. At this time, the liquid temperature during the reaction was 11° C.

The resulting solution contained in the three-neck flask made of glass was transferred into a glove bag so as not to contact with the atmosphere, and after the carbon dioxide concentration in the glove bag became 1 ppm or less, the solution was transferred into a 1 L container made of PFA.
<Evaluation>

In the glove bag in which the carbon dioxide concentration was 1 ppm or less, 30 mL of the resulting tetramethylammonium hypochlorite solution was poured into a fluororesin container, then pH and an active chlorine concentration were evaluated, and it was confirmed that pH was 13.0, and the hypochlorite ion concentration was 1.59 mass %.

Subsequently, 30 mL of the tetramethylammonium hypochlorite solution having been stored in environment of a carbon dioxide concentration of 1 ppm or less and a storage temperature of 23° C. for 10 days was poured into a fluororesin container, and pH and an active chlorine concentration were evaluated. At this time, pH was 13.0, and the hypochlorite ion concentration was 1.59 mass %, so that it was confirmed that the pH and the active chlorine concentration did not largely change.

Examples 2 to 7

In each of Examples 2 to 7, a tetramethylammonium hypochlorite solution was prepared in the same manner as in Example 1, except that (A) mass concentration of TMAH solution, (B) pH of TMAH solution, (C) amount of chlorine fed, (D) feed rate of chlorine, (E) reaction temperature, and (F) carbon dioxide concentration in gas phase were adjusted to the conditions shown in Table 1, and then evaluation was carried out. In Example 7, cooling was not carried out during the reaction, and the reaction temperature rose to 35° C. from 25° C.

Comparative Example 1

In a 2 L glass beaker (manufactured by AS ONE CORPORATION), 233 g of a 25 mass % TMAH aqueous solution having a $CO_2$ content of 2 ppm and 767 g of ion-exchanged water were mixed, thereby obtaining a 5.8 mass % TMAH aqueous solution. The pH at this time, was 13.8. Subsequently, as shown in FIG. 3, a rotor 24 (manufactured by AS ONE CORPORATION, total length 30 mm×diameter 8 mm) was placed in the glass beaker 21, then a thermometer protection tube 22 (manufactured by VIDTEC, bottom seal type) and a thermocouple 23 were introduced, and a tip of a PFA tube 25 (manufactured by FRON INDUSTRY, F-8011-02) having been connected to a chlorine gas container was inserted in the bottom of the solution. At this time, the carbon dioxide concentration in the gas phase portion was 350 ppm.

Thereafter, a magnetic stirrer (manufactured by AS ONE CORPORATION, C-MAG HS10) was set at the lower part of the glass beaker, and while rotating the stirrer at 300 rpm and cooling the outer periphery of the flask with ice water 28, chlorine gas (manufactured by Fujiox Co., Ltd., specification purity 99.4%) was fed at 0.064 Pa·m$^3$/sec (converted value at 0° C.) for 180 minutes, thereby obtaining a tetramethylammonium hypochlorite solution. At this time, the liquid temperature during the reaction was 11° C.

The resulting solution was transferred into a glove bag so as not to come into contact with the atmosphere, and after the carbon dioxide concentration in the glove bag became 1 ppm or less, the solution was transferred into a 1 L container made of PFA.

Comparative Examples 2 to 3

In each of Comparative Examples 2 to 3, a tetramethylammonium hypochlorite solution was prepared in the same manner as in Comparative Example 1, except that (A) mass concentration of tetramethylammonium hydroxide solution, (B) pH of tetramethylammonium hydroxide solution, (C) amount of chlorine fed, (D) feed rate of chlorine, (E) reaction temperature, and (F) carbon dioxide concentration in gas phase were adjusted to the conditions shown in Table 1, and then evaluation was carried out.

The evaluation results are shown in Table 2. In the table, TMAH indicates tetramethylammonium hydroxide.

PORATION, cylindrical vessel C type for reaction 2000 cc) has been processed so as to connect a plurality of half joints 49 made of polytetrafluoroethylene (manufactured by AS ONE CORPORATION, Half Female Joint I type 6 φ), and in the reaction vessel 32, 253 g of a 25 mass % tetramethylammonium hydroxide aqueous solution and 747 g of ultrapure water were mixed, thereby obtaining a 6.3 mass % tetramethylammonium hydroxide aqueous solution. The contents of sodium, potassium, aluminum, magnesium, iron, nickel, copper, silver, cadmium and lead in this tetramethylammonium hydroxide aqueous solution were confirmed to be each less than 1 ppb. The carbon dioxide concentration was 5 ppm (by mass). The pH (23° C.) at this time was 13.8.

At the center of the reaction vessel 32, a stirring bar 37 (manufactured by AS ONE CORPORATION, made of polytetrafluoroethylene (PTFE), equipped with stirring bar/stirring blade, total length 450 mm×diameter 8 mm) was set, and a stirring motor 36 (manufactured by SHINTO Scientific Co., Ltd., Three-one Motor-BLh 600) was installed at

TABLE 1

| | 25% TMAH [g] | Ion-exchanged water [g] | (A) TMAH concentration [mass %] | (B) pH of TMAH | (C) Amount of $Cl_2$ fed [mL] | (D) $Cl_2$ flow rate [Pa · m³/sec] | (E) Reaction Temperature [° C.] | (F) $CO_2$ in gas phase [ppm] | Reaction time [min] |
|---|---|---|---|---|---|---|---|---|---|
| Ex. 1 | 253 | 747 | 6.3 | 13.8 | 6810 | 0.064 | 11 | <1 | 180 |
| Ex. 2 | 233 | 767 | 5.8 | 13.8 | 6810 | 0.064 | 11 | <1 | 180 |
| Ex. 3 | 339 | 661 | 8.5 | 14.0 | 9478 | 0.089 | 5 | <1 | 180 |
| Ex. 4 | 339 | 661 | 8.5 | 14.0 | 9478 | 0.089 | 15 | <1 | 180 |
| Ex. 5 | 253 | 747 | 6.3 | 13.8 | 6810 | 0.064 | 11 | 50 | 180 |
| Ex. 6 | 339 | 661 | 8.5 | 14.0 | 9478 | 0.089 | 25 | <1 | 180 |
| Ex. 7 | 339 | 661 | 8.5 | 14.0 | 9478 | 0.089 | 25→35 (no cooling) | <1 | 180 |
| Comp. Ex. 1 | 233 | 767 | 5.8 | 13.8 | 6810 | 0.064 | 11 | 350 | 180 |
| Comp. Ex. 2 | 192 | 808 | 4.8 | 13.7 | 5892 | 0.055 | 11 | 350 | 180 |
| Comp. Ex. 3 | 253 | 747 | 6.3 | 13.8 | 6810 | 0.064 | 11 | 350 | 180 |

TABLE 2

| | Active chlorine concentration [%] | | Hypochlorite ion concentration [%] | | Hypochlorite ion residual ratio [%] | pH before reaction step | pH immediately after production | pH after 10 days | Storage stability evaluation 1 | Reaction efficiency [%] |
|---|---|---|---|---|---|---|---|---|---|---|
| | Immediately after production | After 10 days | Immediately after production | After 10 days | | | | | | |
| Ex. 1 | 2.18 | 2.18 | 1.59 | 1.59 | 100 | 13.8 | 13.0 | 13.0 | good | 100 |
| Ex. 2 | 2.18 | 2.18 | 1.59 | 1.59 | 100 | 13.8 | 12.0 | 12.0 | good | 100 |
| Ex. 3 | 3.00 | 3.00 | 2.19 | 2.19 | 100 | 14.0 | 13.0 | 13.0 | good | 100 |
| Ex. 4 | 3.00 | 3.00 | 2.19 | 2.19 | 100 | 14.0 | 13.0 | 13.0 | good | 100 |
| Ex. 5 | 2.18 | 2.18 | 1.59 | 1.59 | 100 | 13.8 | 12.5 | 12.5 | good | 100 |
| Ex. 6 | 2.85 | 2.85 | 2.08 | 2.08 | 100 | 14.0 | 13.0 | 13.0 | good | 95 |
| Ex. 7 | 1.74 | 1.74 | 1.27 | 1.27 | 100 | 14.0 | 13.0 | 13.0 | good | 58 |
| Comp. Ex. 1 | 2.13 | 1.02 | 1.55 | 0.74 | 48 | 13.8 | 9.2 | 9.0 | poor | 100 |
| Comp. Ex. 2 | 1.86 | 1.07 | 1.36 | 0.78 | 58 | 13.7 | 9.4 | 9.2 | poor | 100 |
| Comp. Ex.2 | 2.18 | 2.10 | 1.59 | 1.53 | 96 | 13.8 | 10.5 | 10.5 | poor | 100 |

Example 11

<Preparation of Tetramethylammonium Hypochlorite Solution>

As shown in FIG. 2, a reaction vessel 32 was prepared in such manner that a 2 L-volume reaction vessel made of polytetrafluoroethylene (manufactured by AS ONE CORthe upper part of the vessel. In the reaction vessel 32, a thermometer 35 was set so that the temperature during the reaction could be monitored.

A tip of a gas introduction tube 40 made of a tetrafluoroethylene-perfluoro(alkyl vinyl ether) copolymer (manufactured by FRON INDUSTRY, PFA tube) which is capable of switching between chlorine gas (chlorine gas introduction tube 39) and nitrogen gas (nitrogen gas feed tube 41) was inserted in the bottom of the solution (tetramethylammonium hydroxide solution 33).

By way of a chlorine gas exhaust tube 46, one half joint was connected to a chlorine gas trap 47 (manufactured by AS ONE CORPORATION, gas wash bottle) having been filled with a 5 mass % sodium hydroxide aqueous solution.

Furthermore, another half joint and the inlet side of a magnet pump 43 (manufactured by AS ONE CORPORATION, magnet pump whose surface was coated with Teflon (registered trademark)) were connected by way of a tube made of a tetrafluoroethylene-perfluoro(alkyl vinyl ether) copolymer (manufactured by FRON INDUSTRY, PFA tube) that was a reaction solution transfer tube 42, and then the outlet side of the pump was connected by way of a filtration filter 44 (manufactured by Nihon Entegris G.K., Fluoroguard AT, pore diameter 0.1 µm) and a reaction solution return tube 45 made of the same material as that of the reaction solution transfer tube 42.

Next, nitrogen gas having a carbon dioxide concentration of less than 1 ppm was allowed to flow through the nitrogen gas feed tube 41 and the gas feed tube 40 (tube made of a tetrafluoroethylene-perfluoro(alkyl vinyl ether) copolymer (manufactured by FRON INDUSTRY, PFA tube)) at 0.29 Pa·m$^3$/sec for 20 minutes, whereby carbon dioxide in the gas phase portion in the reaction vessel 32 was purged.

Thereafter, the stirring motor 36 was rotated at 300 rpm, and while cooling the outer periphery of the reaction vessel 32 in a reaction bath 48 (ice water), chlorine gas (commercial product, specification purity 99.999%, water content 0.5 ppm (by mass) or less, carbon dioxide 1 ppm (by mass) or less) was fed at 0.064 Pa·m$^3$/sec for 180 minutes, thereby obtaining a tetramethylammonium hypochlorite aqueous solution (total amount of chlorine gas used 6810 mL). At this time, the liquid temperature during the reaction was 11° C. When the reaction was carried out while feeding chlorine gas, the pump 43 was started, and a tetramethylammonium hypochlorite aqueous solution was produced while carrying out filtration operation (even in the case where pH of the reaction solution became 13.5 or less (23° C.), filtration operation was continued).

pH and hypochlorite ion concentration of the resulting tetramethylammonium hypochlorite aqueous solution were evaluated, and as a result, pH was 13.0, and the hypochlorite ion concentration was 1.59 mass %. Subsequently, metal concentrations in the tetramethylammonium hypochlorite aqueous solution were measured in accordance with <Measuring method for metal atom concentrations in quaternary alkylammonium hypochlorite solution>, and as a result, the contents of metals were each less than 1 ppm. The results are shown in Table 4.

Examples 12 and 13

In each of Examples 12 and 13, a tetramethylammonium hypochlorite aqueous solution was produced in the same manner as in Example 11, except that the condition of Table 3, that is, (A) mass concentration of TMAH solution (with the proviso that a solution in which the contents of sodium, potassium, aluminum, magnesium, iron, nickel, copper, silver, cadmium and lead were each less than 1 ppb and the carbon dioxide content was 2 ppm was used) was adjusted to the condition shown in Table 3, and then the metal contents were examined.

In Example 12, after the total chlorine gas was fed, feeding of chlorine gas was terminated, and then the pump 43 was started to carry out filtration operation. In Example 13, filtration operation was not carried out. The results are shown in Table 4.

Comparative Example 11

A tetramethylammonium hypochlorite aqueous solution was produced in the same manner as in Example 11, except that as the reaction vessel 32, a 1000 mL reaction vessel made of glass (manufactured by SIBATA SCIENTIFIC TECHNOLOGY LTD., 1 L separable reaction vessel) and joined with a worked bypass tube made of glass and having a ground size of 19/38 mm was used. In Comparative Example 11, filtration was carried out during the production. The conditions are shown in Table 3, and the results are shown in Table 4.

Comparative Example 12

Using a 1000 mL three-neck flask made of glass (manufactured by AS ONE CORPORATION, 3-Neck Glass Flask) as the reaction vessel 32, a tetramethylammonium hypochlorite aqueous solution was produced under the conditions shown in Table 3. Other conditions were in conformity with those in Example 12. Filtration was carried out under the same conditions as in Example 12. The results are shown in Table 4.

Comparative Example 13

A tetramethylammonium hypochlorite aqueous solution was produced under the conditions shown in Table 3, except that as the reaction vessel 32, a 1000 mL three-neck flask made of glass (manufactured by AS ONE CORPORATION, 3-Neck Glass Flask) was used. Other conditions were in conformity with those in Example 13. The results are shown in Table 4.

TABLE 3

|   | (A) TMAH concentration [mass %] | (B) pH of TMAH | (C) Amount of Cl$_2$ fed [mL] | (D) Cl$_2$ flow rate [Pa · m$^3$/sec] | (E) Reaction temperature [° C.] | Reaction vessel | Filtration |
|---|---|---|---|---|---|---|---|
| Ex. 11 | 6.3 | 13.8 | 6810 | 0.064 | 11 | PFA | during production |
| Ex. 12 | 5.8 | 13.8 | 6810 | 0.064 | 11 | PFA | after production |
| Ex. 13 | 5.8 | 13.8 | 6810 | 0.064 | 11 | PFA | none |
| Comp. Ex. 11 | 6.3 | 13.8 | 6810 | 0.064 | 11 | glass | during production |
| Comp. Ex. 12 | 4.8 | 13.7 | 5892 | 0.055 | 11 | glass | after production |

TABLE 3-continued

| | (A) TMAH concentration [mass %] | (B) pH of TMAH | (C) Amount of Cl$_2$ fed [mL] | (D) Cl$_2$ flow rate [Pa · m$^3$/sec] | (E) Reaction temperature [° C.] | Reaction vessel | Filtration |
|---|---|---|---|---|---|---|---|
| Comp. Ex. 13 | 5.8 | 13.8 | 6810 | 0.064 | 11 | glass | none |

TABLE 4

| | Active chlorine concentration (mass %) Immediately after production | Hypochlorite ion concentration (mass %) Immediately after production | pH (after production) | Metal impurity concentration (ppb) | | | | | | | | | |
|---|---|---|---|---|---|---|---|---|---|---|---|---|---|
| | | | | Na | K | Al | Mg | Fe | Ni | Cu | Ag | Cd | Pb |
| Ex. 11 | 2.18 | 1.59 | 13.0 | <1 | <1 | <1 | <1 | <1 | <1 | <1 | <1 | <1 | <1 |
| Ex. 12 | 2.18 | 1.59 | 12.0 | <1 | <1 | <1 | <1 | <1 | <1 | <1 | <1 | <1 | <1 |
| Ex. 13 | 2.18 | 1.59 | 12.0 | <1 | <1 | <1 | 13 | 6 | 10 | 3 | 3 | 3 | 3 |
| Comp. Ex. 11 | 2.18 | 1.59 | 13.0 | 210 | 25 | 49 | <1 | <1 | <1 | <1 | <1 | <1 | <1 |
| Comp. Ex. 12 | 1.86 | 1.36 | 10.2 | 105 | 16 | 30 | <1 | <1 | <1 | <1 | <1 | <1 | <1 |
| Comp. Ex. 13 | 2.18 | 1.59 | 12.0 | 220 | 24 | 55 | 20 | 9 | 11 | 3 | 3 | 3 | 3 |

Example 14

To 100 mL of the tetramethylammonium hypochlorite aqueous solution obtained in Example 11, 0.8 mL of 34.0 mass % high-purity hydrochloric acid was added, thereby adjusting pH (23° C.) to 9.6 (prepared in container made of PFA). The contents of sodium, potassium, aluminum, magnesium, iron, nickel, copper, silver, cadmium and lead in the resulting tetramethylammonium hypochlorite aqueous solution were confirmed to be each less than 1 ppb.

<Evaluation of Ruthenium Etching Performance>

An oxide film was formed on a silicon wafer using a batch type thermal oxidation furnace, and thereon, a ruthenium film of 1000 Å (±10%) was formed using a sputtering method. A sheet resistivity was measured by a four-probe resistivity measuring device (Loresta-GP, manufactured by Mitsubishi Chemical Analytech Co., Ltd.), and it was converted into a film thickness.

In a beaker (beaker made of PFA), 30 ml of the tetramethylammonium hypochlorite aqueous solution of pH 9.6 obtained in Example 14 was placed, and each sample piece of 10×20 mm was immersed in the cleaning liquid for 1 minute, and a value obtained by dividing a change in film thickness between before and after the processing by the immersion time was determined as an etching rate, and as a result, the etching rate was 100 Å/min or more.

Example 21

A tetramethylammonium hypochlorite solution was obtained in the same manner as in Example 1. The resulting aqueous solution contained in the three-neck flask made of glass was transferred into a glove bag so as not to contact with the atmosphere, and after the carbon dioxide concentration in the glove bag became 1 ppm or less, the solution was transferred into a 1 L PFA container.

In the glove bag in which the carbon dioxide concentration was 1 ppm or less, 30 mL of the resulting tetramethylammonium hypochlorite solution was poured into a container made of PFA, and pH immediately after the production was measured using the aforesaid "pH measuring method" and an active chlorine concentration immediately after the production was measured using the aforesaid "Calculation method for active chlorine concentration and hypochlorite ion concentration". The pH of the resulting tetramethylammonium hypochlorite solution was 13.0, and the active chlorine concentration thereof was 2.18 mass %.

<Evaluation Method 2 for Storage Stability>

Subsequently, pH and an active chlorine concentration of the tetramethylammonium hypochlorite solution having been stored for 30 days in environment of a carbon dioxide concentration of 1 ppm or less and a storage temperature of 23° C. were evaluated, and as a result, the pH was 13.0, and the active chlorine concentration was 2.18 mass %, so that it was confirmed that they did not change with time.

To each of the tetramethylammonium hypochlorite solutions immediately after the production and after the elapse of storage of 30 days, 8.8 mL of 35 mass % high-purity hydrochloric acid for semiconductor (manufactured by KANTO CHEMICAL CO., INC., high-purity reagent Ultra-pure HCl) was added, and they were each stirred and diluted in such a manner that the pH became 9.5.

pH of the resulting tetramethylammonium hypochlorite solution after dilution was measured, and as a result, the pH was 9.5. Further, an active chlorine concentration was measured, and as a result, the active chlorine concentration was 2.18 mass %, so that it was confirmed that there was no change between before and after the dilution.

The tetramethylammonium hypochlorite solution having been diluted so as to have pH of 9.5 was evaluated on the etching rate using the aforesaid calculation method for etching rate of ruthenium, and as a result, the etching rate was 100 Å/min or more.

Examples 22 to 27, Comparative Example 21, Reference Example

In Examples 22 to 27, Comparative Example 21 and Reference Example, preparation and evaluation were carried out in the same manner as in Example 21, except that (A) mass concentration of tetramethylammonium hydroxide (TMAH) solution, (B) pH of TMAH solution, (F) diluent solution, (G) concentration of diluent solution, and (H) amount of diluent solution added were changed to the conditions shown in Table 5. When pH of the tetramethylammonium hypochlorite aqueous solution after the elapse of storage of 30 days was 10 or less, the etching rate was evaluated using the calculation method for etching rate of ruthenium without carrying out dilution of the tetramethylammonium hypochlorite aqueous solution. The results obtained are shown in Table 6.

Example 28

A tetramethylammonium hypochlorite solution was obtained in the same manner as in Reference Example. The resulting aqueous solution contained in the three-neck flask made of glass was transferred into a glove bag so as not to contact with the atmosphere, and after the carbon dioxide concentration in the glove bag became 1 ppm or less, the solution was transferred into a 1 L PFA container.

In the glove bag, 100 mL of 35 mass % high-purity hydrochloric acid for semiconductor was added to 1000 g of the tetramethylammonium hypochlorite solution, and they were stirred. Using the aforesaid "pH measuring method", pH was measured, and using the aforesaid "Calculation method for active chlorine concentration and hypochlorite ion concentration", an active chlorine concentration was measured. The pH of the resulting tetramethylammonium hypochlorite solution was 13.0, and the active chlorine concentration thereof was 1.98 mass %.

Subsequently, pH and an active chlorine concentration of the tetramethylammonium hypochlorite solution having been stored for 30 days in environment of a carbon dioxide concentration of 1 ppm or less and a storage temperature of 23° C. were evaluated, and as a result, pH was 13.0, and the active chlorine concentration was 1.98 mass %, so that it was confirmed that they did not change with time.

To the tetramethylammonium hypochlorite solution, 8.8 mL of 35 mass % high-purity hydrochloric acid for semiconductor was added, and they were stirred.

pH of the resulting tetramethylammonium hypochlorite solution after dilution was measured, and as a result, the pH was 9.5. Further, an active chlorine concentration was measured, and as a result, the active chlorine concentration was 1.98 mass %, so that it was confirmed that there was no change between before and after the dilution.

The tetramethylammonium hypochlorite solution having been diluted so as to have pH of 9.5 was evaluated on the etching rate using the aforesaid calculation method for etching rate of ruthenium, and as a result, the etching rate was 100 Å/min or more.

TABLE 5

| | 25% TMAH [g] | Ion-exchanged water [g] | (A) TMAH concentration [mass %] | (B) pH of TMAH | (C) Amount of Cl$_2$ fed [mL] | (D) Cl$_2$ flow rate [Pa·m$^3$/sec] | (E) Reaction Temperature [° C.] | Reaction time [min] | (F) Diluent solution | (G) Diluent solution concentration [%] | (H) Amount of diluent solution added [mL] |
|---|---|---|---|---|---|---|---|---|---|---|---|
| Ex. 21 | 253 | 747 | 6.3 | 13.8 | 6810 | 0.064 | 11 | 180 | hydrochloric acid | 35.0 | 8.8 |
| Ex. 22 | 244 | 756 | 6.1 | 13.8 | 6810 | 0.064 | 11 | 180 | hydrochloric acid | 35.0 | 2.8 |
| Ex. 23 | 264 | 736 | 6.6 | 13.9 | 6810 | 0.064 | 11 | 180 | hydrochloric acid | 35.0 | 28 |
| Ex. 24 | 253 | 747 | 6.3 | 13.8 | 6810 | 0.064 | 11 | 180 | nitric acid | 70.0 | 10 |
| Ex. 25 | 253 | 747 | 6.3 | 13.8 | 6810 | 0.064 | 11 | 180 | acetic acid | 100.0 | 5.7 |
| Ex. 26 | 253 | 747 | 6.3 | 13.8 | 6810 | 0.064 | 11 | 180 | hydrochloric acid | 35.0 | 8.5 |
| Ex. 27 | 253 | 747 | 6.3 | 13.8 | 6810 | 0.064 | 11 | 180 | hydrochloric acid | 35.0 | 8.7 |
| Ex. 28 | 640 | 360 | 16.0 | 14.2 | 6810 | 0.064 | 11 | 180 | hydrochloric acid | 35.0 | 8.8 |
| Comp. Ex. 21 | 233 | 767 | 5.8 | 13.8 | 6810 | 0.064 | 11 | 180 | — | — | — |
| Ref. Ex. | 640 | 360 | 16.0 | 14.2 | 6810 | 0.064 | 11 | 180 | nitric acid | 70.0 | 10 |

TABLE 6

| | Active chlorine concentration [mass %] | | | Hypochlorite ion concentration [mass %] | | Hypochlorite ion residual ratio after 30 days [%] | pH | | | | Ru etching evaluation [Å/min] | Storage stability evaluation |
|---|---|---|---|---|---|---|---|---|---|---|---|---|
| | Immediately after production | After 30 days | After dilution | Immediately after production | After 30 days | | Immediately after production | During storage | After 30 days | After dilution (when used) | | |
| Ex. 21 | 2.18 | 2.18 | 2.18 | 1.59 | 1.59 | 100 | 13.0 | 13.0 | 13.0 | 9.5 | 346 good | good |
| Ex. 22 | 2.18 | 2.18 | 2.18 | 1.59 | 1.59 | 100 | 12.5 | 12.5 | 12.5 | 9.5 | 344 good | good |
| Ex. 23 | 2.17 | 2.17 | 2.17 | 1.58 | 1.58 | 100 | 13.5 | 13.5 | 13.5 | 9.5 | 343 good | good |
| Ex. 24 | 2.18 | 2.18 | 2.18 | 1.59 | 1.59 | 100 | 13.0 | 13.0 | 13.0 | 9.5 | 341 good | good |
| Ex. 25 | 2.18 | 2.18 | 2.18 | 1.59 | 1.59 | 100 | 13.0 | 13.0 | 13.0 | 9.5 | 342 good | good |
| Ex. 26 | 2.18 | 2.18 | 2.18 | 1.59 | 1.59 | 100 | 13.0 | 13.0 | 13.0 | 11.0 | 19 good | good |
| Ex. 27 | 2.18 | 2.18 | 2.18 | 1.59 | 1.59 | 100 | 13.0 | 13.0 | 13.0 | 10.5 | 53 good | good |
| Ex. 28 | 2.18 | 1.98 | 1.98 | 1.45 | 1.45 | 100 | >14.0 | 13.0 | 13.0 | 9.5 | 300 good | good |
| Comp. Ex. 21 | 2.13 | 0.75 | — | 1.55 | 0.55 | 35 | 9.5 | 9.5 | 9.1 | 9.1 | 65 poor | poor |
| Ref. Ex. | 2.18 | 0.00 | — | 1.59 | 0.00 | 0 | >14.0 | >14.0 | >14.0 | 9.5 | 0 poor | poor |

REFERENCE SIGNS LIST 10 ice water
11 three-neck flask
12 thermometer protection tube
13 thermocouple
14 rotor
15 tube made of PFA
16 gas wash bottle
17 5 mass % sodium hydroxide aqueous solution
18 flowmeter
19 water bath
21 glass beaker
22 thermometer protection tube
23 thermocouple
24 rotor
25 tube made of PFA
26 flowmeter
27 water bath
28 ice water
31 reaction device
32 reaction vessel
33 quaternary alkylammonium hydroxide solution (before reaction)
34 inner surface of reaction vessel
35 thermometer
36 stirring motor
37 stirring bar
38 stirring blade
39 chlorine gas feed tube
40 gas introduction tube
41 nitrogen gas feed tube
42 reaction solution transfer tube
43 pump
44 filtration filter
45 reaction solution return tube
46 chlorine gas exhaust tube
47 chlorine gas trap
48 reaction bath
49 half joint

The invention claimed is:

1. A method for producing a quaternary alkylammonium hypochlorite solution, comprising:
    a preparation step of preparing a quaternary alkylammonium hydroxide solution; and
    a reaction step of bringing the quaternary alkylammonium hydroxide solution into contact with chlorine; wherein
    a carbon dioxide concentration in a gas phase portion in the reaction step is 100 ppm by volume or less, and pH of a liquid phase portion in the reaction step is 10.5 or more.

2. The method according to claim 1, wherein the quaternary alkylammonium hydroxide solution prepared in the preparation step is a solution of quaternary alkylammonium hydroxide, in which the number of carbon atoms of an alkyl group of the quaternary alkylammonium hydroxide is 1 to 10.

3. The method according to claim 1, wherein in the reaction step, a reaction temperature is −35° C. or higher and 15° C. or lower.

4. The method according to claim 1, wherein in the reaction step, a carbon dioxide concentration in the quaternary alkylammonium hydroxide solution is 500 ppm or less.

5. A method for producing a quaternary alkylammonium hypochlorite solution, comprising a reaction step of bringing a quaternary alkylammonium hydroxide solution into contact with chlorine gas in a reaction vessel, wherein
    an inner surface of the reaction vessel, that contacts with the quaternary alkylammonium hydroxide solution, is formed of an organic polymer material.

6. The method according to claim 5, wherein the organic polymer material is a fluororesin.

7. The method according to claim 5, wherein a water content in the chlorine gas is 10 ppm by volume or less.

8. The method according to claim 1, further comprising a step of filtering a quaternary alkylammonium hypochlorite solution obtained in the reaction step.

9. The method according to claim 8, wherein pH of the quaternary alkylammonium hypochlorite solution at 25° C., the solution being to be filtered, is 13.5 or less.

10. The method according to claim 9, wherein pH of the quaternary alkylammonium hypochlorite solution at 25° C., the solution being to be filtered, is 12.5 or less.

11. The method according to claim 1, comprising a storage step of storing a reaction solution after the reaction step, wherein in the storage step, pH of the quaternary alkylammonium hypochlorite solution at 25° C. is adjusted to 12.0 or more and less than 14.0.

12. The method according to claim 11, comprising a dilution step of adjusting pH of the reaction solution after the storage step, wherein in the dilution step, pH of the quaternary alkylammonium hypochlorite solution at 25° C. is adjusted to 8.0 or more and less than 12.0.

13. The method according to claim 12, wherein the dilution step is a step of diluting the stored quaternary alkylammonium hypochlorite solution with a solution having pH of more than 0 and 7 or less at 25° C.

14. A processing method for a semiconductor wafer, comprising:
    preparing a quaternary alkylammonium hypochlorite solution according to claim 1; and
    processing a semiconductor wafer surface by the quaternary alkylammonium hypochlorite solution.

15. The processing method according to claim 14, wherein the semiconductor wafer contains at least one selected from the group consisting of copper, tungsten, tantalum, titanium, cobalt, ruthenium, manganese, aluminum, silicon, silicon oxide, and compounds thereof.

16. A quaternary alkylammonium hypochlorite solution, wherein a content of each metal of sodium, potassium and aluminum is less than 1 ppb.

17. The quaternary alkylammonium hypochlorite solution according to claim 16, wherein, a content of each metal of magnesium, iron, nickel, copper, silver, cadmium and lead is less than 1 ppb.

18. The quaternary alkylammonium hypochlorite solution according to claim 16, having pH of 9.0 or more and 12.5 or less at 23° C.

* * * * *